US012605055B2

(12) United States Patent (10) Patent No.: US 12,605,055 B2
Kitahara (45) Date of Patent: Apr. 21, 2026

(54) MEDICAL APPARATUS AND METHOD FOR OPERATING MEDICAL APPARATUS

(71) Applicant: FUJIFILM Corporation, Tokyo (JP)

(72) Inventor: Masahiro Kitahara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 400 days.

(21) Appl. No.: 18/322,559

(22) Filed: May 23, 2023

(65) Prior Publication Data

US 2023/0320578 A1 Oct. 12, 2023

Related U.S. Application Data

(63) Continuation of application No. PCT/JP2021/035098, filed on Sep. 24, 2021.

(30) Foreign Application Priority Data

Nov. 24, 2020 (JP) ................................ 2020-194753

(51) Int. Cl.
*A61B 5/1455* (2006.01)
*A61B 1/00* (2006.01)
*A61B 1/045* (2006.01)
*A61B 1/06* (2006.01)
*A61B 5/00* (2006.01)

(52) U.S. Cl.
CPC .......... *A61B 1/0638* (2013.01); *A61B 1/0005* (2013.01); *A61B 1/045* (2013.01); *A61B 5/0071* (2013.01); *A61B 5/14552* (2013.01)

(58) Field of Classification Search
CPC ...................................................... A61B 5/1455
See application file for complete search history.

(56) References Cited

U.S. PATENT DOCUMENTS

| | | | |
|---|---|---|---|
| 10,992,922 | B2 | 4/2021 | Liu |
| 11,190,752 | B2 | 11/2021 | Liu |
| 2007/0203413 | A1 | 8/2007 | Frangioni |
| 2008/0177140 | A1 | 7/2008 | Cline et al. |
| 2017/0135555 | A1 | 5/2017 | Yoshizaki |

(Continued)

FOREIGN PATENT DOCUMENTS

| | | |
|---|---|---|
| JP | 2010268838 | 12/2010 |
| JP | 2012152460 | 8/2012 |

(Continued)

OTHER PUBLICATIONS

"Search Report of Europe Counterpart Application", issued on Jul. 5, 2024, p. 1-p. 9.

(Continued)

*Primary Examiner* — Marjan Fardanesh
(74) *Attorney, Agent, or Firm* — JCIPRNET

(57) ABSTRACT

The medical apparatus is a medical apparatus for illuminating a subject and capturing an image of reflected light from the subject and includes: a light source configured to emit illumination light including a first wavelength range; a light receiving section having a first channel for sensing a first sensing range; and an image control processor, in which the first sensing range is a wavelength range that does not overlap with the first wavelength range or overlaps with the first wavelength range up to a half wavelength, and the image control processor is configured to acquire at least one or more examination images based on light included in the first sensing range sensed by the first channel.

14 Claims, 18 Drawing Sheets

(56) References Cited

U.S. PATENT DOCUMENTS

| 2017/0224205 A1 | 8/2017 | Sunar et al. |
| 2018/0270474 A1 | 9/2018 | Liu |
| 2020/0060551 A1 | 2/2020 | Kajita et al. |
| 2021/0169305 A1 | 6/2021 | Fukazawa et al. |
| 2022/0086416 A1 | 3/2022 | Liu |

FOREIGN PATENT DOCUMENTS

| JP | 2018514748 | 6/2018 |
| WO | 2017085793 | 5/2017 |
| WO | 2019092950 | 5/2019 |

OTHER PUBLICATIONS

"International Search Report (Form PCT/ISA/210) of PCT/JP2021/035098", mailed on Dec. 7, 2021, with English translation thereof, pp. 1-5.
"Written Opinion of the International Searching Authority (Form PCT/ISA/237) of PCT/JP2021/035098", mailed on Dec. 7, 2021, with English translation thereof, pp. 1-8.

10

12

15

LIGHT RECEIVING SECTION

~24

14

LIGHT SOURCE DEVICE

LIGHT SOURCE UNIT ~20

LIGHT SOURCE CONTROL UNIT ~22

16

PROCESSOR DEVICE

CONTROL UNIT ~59

IMAGE PROCESSING UNIT ~61

DISPLAY CONTROL UNIT ~66

18~ DISPLAY

19~ CONSOLE

EMISSION SPECTRUM

LARGE

AMOUNT OF LIGHT

SMALL 380   430   480   530   580   630   680   730   780   830   880

WAVELENGTH (nm)

SPECTRA OF EXCITATION LIGHT AND
FLUORESCENCE OF INDOCYANINE GREEN

FLUORESCENCE SPECTRUM

ABSORPTION SPECTRA OF HEMOGLOBIN

CHARACTERISTICS OF
FIRST SPECTRAL ELEMENT

REFLECTANCE (%)

100

0

FIRST
SPECTRAL
RANGE

λ−X    λ    λ+Y    WAVELENGTH (nm)

CHARACTERISTICS OF
FIRST SPECTRAL ELEMENT

TRANSMITTANCE (%)

100

0

SECOND SPECTRAL RANGE

λ−X    λ    λ+Y    WAVELENGTH (nm)

FIRST SPECTRAL RANGE

SECOND SPECTRAL RANGE

FIG. 13

FIRST SENSING RANGE

FIG. 14

SECOND SENSING RANGE

FIG. 21

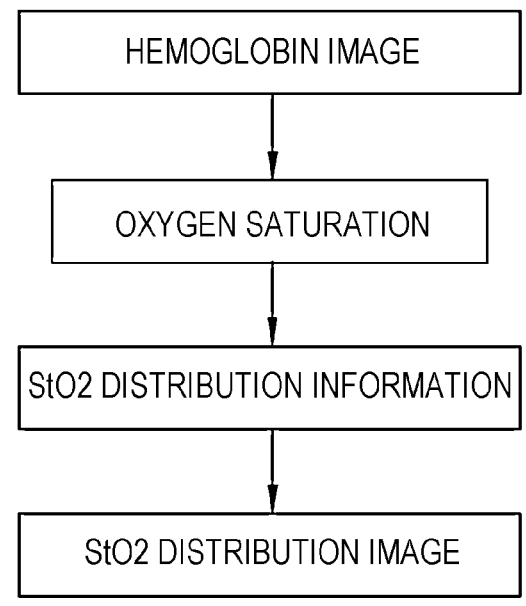

```
┌─────────────────────────────────┐
│        HEMOGLOBIN IMAGE         │
└─────────────────────────────────┘
                │
                ▼
┌─────────────────────────────────┐
│        OXYGEN SATURATION        │
└─────────────────────────────────┘
                │
                ▼
┌─────────────────────────────────┐
│   StO2 DISTRIBUTION INFORMATION │
└─────────────────────────────────┘
                │
                ▼
┌─────────────────────────────────┐
│      StO2 DISTRIBUTION IMAGE    │
└─────────────────────────────────┘
```

FIG. 22

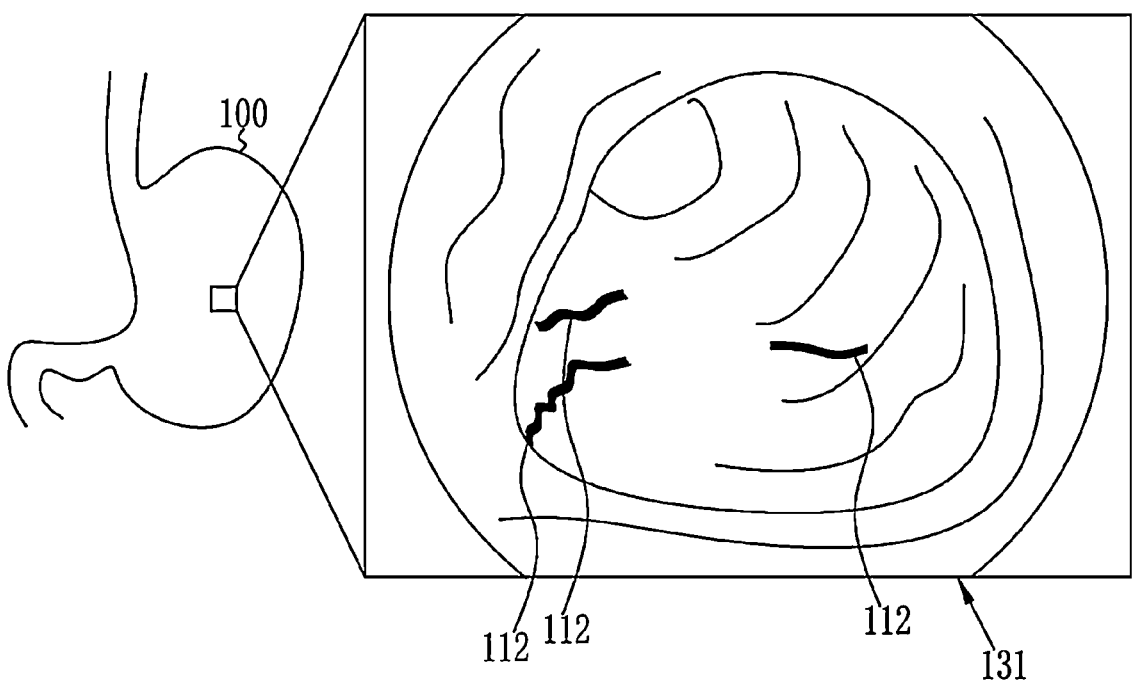

FLUORESCENT LYMPHATIC-VESSEL IMAGE ~82

↓

LYMPHATIC-VESSEL DISTRIBUTION INFORMATION

NORMAL-LIGHT IMAGE ~130

↓

LYMPHATIC-VESSEL SUPERIMPOSED IMAGE ~132

114  114

100

112  112

112

133

MEDICAL APPARATUS AND METHOD FOR OPERATING MEDICAL APPARATUS

CROSS-REFERENCE TO RELATED APPLICATIONS

This application is a Continuation of PCT International Application No. PCT/JP2021/035098 filed on 24 Sep. 2021, which claims priority under 35 U.S.C § 119 (a) to Japanese Patent Application No. 2020-194753 filed on 24 Nov. 2020. The above application is hereby expressly incorporated by reference, in its entirety, into the present application.

BACKGROUND OF THE INVENTION

1. Field of the Invention

The present invention relates to a medical apparatus for acquiring a plurality of types of images and a method for operating the medical apparatus.

2. Description of the Related Art

In the medical field, a medical apparatus including a light source device, an endoscope, and a processor device is widely used. In the field of a medical apparatus, especially an endoscope, a subject is illuminated, and an image of reflected light from the subject is captured. In an endoscope system, the subject is illuminated with white light including red light, green light, and blue light to obtain an image for visually observing the subject.

In addition, an endoscope has been developed in which a fluorescent substance such as indocyanine green, which is a fluorescent substance that binds to lipoproteins in blood or lymph, is administered to a blood vessel or a lymph node, a subject is illuminated with excitation light of the fluorescent substance, and an image of fluorescence emitted by the fluorescent substance is captured to visualize the blood vessel or the lymph vessel, thereby obtaining a fluorescence image for observing an infiltration range of cancer or blood flow failure.

Furthermore, an image (blue oxygen saturation image) indicating the oxygen saturation of a subject can be obtained by illuminating the subject with near-ultraviolet light and capturing an image of the subject using the property that the absorption coefficients of oxyhemoglobin and deoxyhemoglobin in blood differ depending on the wavelength range of illumination light. In addition, an endoscope capable of obtaining an image (red oxygen saturation image) indicating the oxygen saturation of a subject by illuminating the subject with near-infrared light and capturing an image has also been developed.

JP2010-268838A describes an endoscope system in which, in order to obtain both an observation image and a red oxygen saturation image, laser diodes that respectively emit visible light, laser light of 700 nm, and laser light of 980 nm are provided, and a subject is irradiated with the light as a type of irradiation light. JP2010-268838A also describes a configuration in which reflected light from the subject is separated (spectrally divided) into light in a range for obtaining the observation image and light in a range for obtaining the red oxygen saturation image (illumination light for oxygen saturation), and the respective types of light are made to enter different imaging elements to capture the images.

SUMMARY OF THE INVENTION

In the medical field, as described above, there is a demand for obtaining both a fluorescence image based on fluorescence emitted from a fluorescent substance by excitation light and an oxygen saturation image based on illumination light for oxygen saturation (see JP2010-268838A), and utilizing the images for diagnosis of a lesion or the like. There has been a demand for a medical apparatus capable of acquiring a plurality of examination images such as the fluorescence image and the oxygen saturation image, and achieving cost reduction and suppression of the number of components as much as possible.

An object of the present invention is to provide a medical apparatus capable of acquiring a plurality of examination images and achieving cost reduction and suppression of the number of components as much as possible, and a method for operating the medical apparatus.

A medical apparatus according to the present invention is a medical apparatus for illuminating a subject and capturing an image of reflected light from the subject, and the medical apparatus includes: a light source configured to emit illumination light including a first wavelength range; a light receiving section having a first channel for sensing a first sensing range; and an image control processor. The first sensing range is a wavelength range that does not overlap with the first wavelength range or overlaps with the first wavelength range up to a half wavelength. The image control processor is configured to acquire at least one or more examination images based on light included in the first sensing range.

It is preferable that the reflected light include the first wavelength range and a second wavelength range that is a wavelength range different from the first wavelength range, the light receiving section have a second channel for sensing a second sensing range that is a wavelength range different from the first sensing range, and the second sensing range be a wavelength range that does not overlap with the second wavelength range or overlaps with the second wavelength range up to a half wavelength.

It is preferable that the light receiving section have a first spectral element that spectrally divides the reflected light into a first spectral range and a second spectral range different from the first spectral range, a first imaging element having a first transmission range, and a second imaging element having a second transmission range different from the first transmission range, the first sensing range be a range based on the first spectral range and the first transmission range, and the second sensing range be a range based on the second spectral range and the second transmission range. It is preferable that the second transmission range include a second transmission range A, a second transmission range B, and a second transmission range C, which are different from each other.

It is preferable that the first wavelength range be a wavelength range necessary for excitation of a fluorescent substance and calculation of oxygen saturation based on a difference in responsiveness to the illumination light between oxyhemoglobin and deoxyhemoglobin, the first sensing range be a wavelength range including a wavelength range of fluorescence emitted from the fluorescent substance, and the second sensing range be a wavelength range including the wavelength range necessary for calculation of oxygen saturation.

It is preferable that the fluorescent substance receive light including the first wavelength range and emit fluorescence that is light in the second wavelength range, the first channel be configured to sense the fluorescence, and the image control processor be configured to acquire a fluorescent blood-vessel image based on the fluorescence and a fluorescent lymphatic-vessel image based on the fluorescence as the at least one or more examination images, and acquire blood-vessel distribution information from the fluorescent blood-vessel image and lymphatic-vessel distribution information from the fluorescent lymphatic-vessel image. It is preferable that the image control processor be configured to acquire a hemoglobin image based on light in the wavelength range necessary for calculation of oxygen saturation as the at least one or more examination images, calculate the oxygen saturation from the hemoglobin image, and calculate StO2 distribution information from the oxygen saturation.

It is preferable that the light source be configured to emit normal light, the light receiving section be configured to sense the reflected light obtained by irradiating the subject with the normal light, and the image control processor be configured to acquire a normal-light image based on the normal light, and generate at least one of a blood-vessel superimposed image in which the blood-vessel distribution information is superimposed on the normal-light image, a lymphatic-vessel superimposed image in which the lymphatic-vessel distribution information is superimposed on the normal-light image, or a vessel superimposed image in which the blood-vessel distribution information and the lymphatic-vessel distribution information are superimposed on the normal-light image.

It is preferable that the light receiving section be configured to sense the wavelength range necessary for calculation of oxygen saturation and the wavelength range of the fluorescence, and the image control processor be configured to acquire a hemoglobin image based on light in the wavelength range necessary for calculation of oxygen saturation and a fluorescent blood-vessel image based on the fluorescence as the at least one or more examination images, calculate the oxygen saturation from the hemoglobin image, acquire StO2 distribution information from the oxygen saturation, acquire blood-vessel distribution information from the fluorescent blood-vessel image, and acquire blood-vessel visualized StO2 information from the blood-vessel distribution information and the StO2 distribution information. It is preferable that the light source be configured to emit normal light, the light receiving section be configured to sense the reflected light obtained by irradiating the subject with the normal light, and the image control processor be configured to acquire a normal-light image based on the normal light, and superimpose the blood-vessel visualized StO2 information on the normal-light image to generate a blood-vessel visualized StO2 image.

It is preferable that the light source be configured to emit light in the wavelength range necessary for excitation of a fluorescent substance and calculation of oxygen saturation and normal light, and the image control processor be configured to acquire a fluorescent blood-vessel image based on the fluorescence, a fluorescent lymphatic-vessel image based on the fluorescence, a hemoglobin image based on the light in the wavelength range necessary for calculation of oxygen saturation, and a normal-light image based on the normal light as the at least one or more examination images, calculate the oxygen saturation from the hemoglobin image, acquire StO2 distribution information from the oxygen saturation, acquire blood-vessel distribution information from the fluorescent blood-vessel image and lymphatic-vessel distribution information from the fluorescent lymphatic-vessel image, acquire blood-vessel visualized StO2 information from the blood-vessel distribution information and the oxygen saturation, and superimpose the blood-vessel visualized StO2 information and the lymphatic-vessel distribution information on the normal-light image to generate a vessel visualized StO2 image.

It is preferable that the light receiving section have a second spectral element that spectrally divides the reflected light into at least two or more types of light having a same wavelength range, a first optical element that cuts a first cut wavelength included in the light spectrally divided by the second spectral element to obtain a first dispersion range, a first imaging element having a first transmission range, a second optical element that cuts a second cut wavelength included in the light spectrally divided by the second spectral element and different from the first cut wavelength to obtain a second dispersion range different from the first dispersion range, and a second imaging element having a second transmission range, the first sensing range be a range based on the first dispersion range and the first transmission range, and the second sensing range be a range based on the second dispersion range and the second transmission range. It is preferable that the light receiving section have one sensor provided with a first filter corresponding to the first channel and a second filter corresponding to the second channel.

A method for operating a medical apparatus is a method for operating a medical apparatus for illuminating a subject and capturing an image of reflected light from the subject, in which a light source is configured to emit illumination light including a first wavelength range. A light receiving section has a first channel for sensing a first sensing range. An image control processor acquires at least one or more examination images based on light included in the first sensing range sensed by the first channel. The first sensing range is a wavelength range that does not overlap with the first wavelength range or overlaps with the first wavelength range up to a half wavelength.

According to the medical apparatus and the method for operating the medical apparatus of the present invention, it is possible to provide a medical apparatus capable of acquiring a plurality of examination images and achieving cost reduction and suppression of the number of components as much as possible.

BRIEF DESCRIPTION OF THE DRAWINGS

FIG. 13 is a graph illustrating a first sensing range;

FIG. 14 is a graph illustrating a second sensing range;

5

Figure 15:
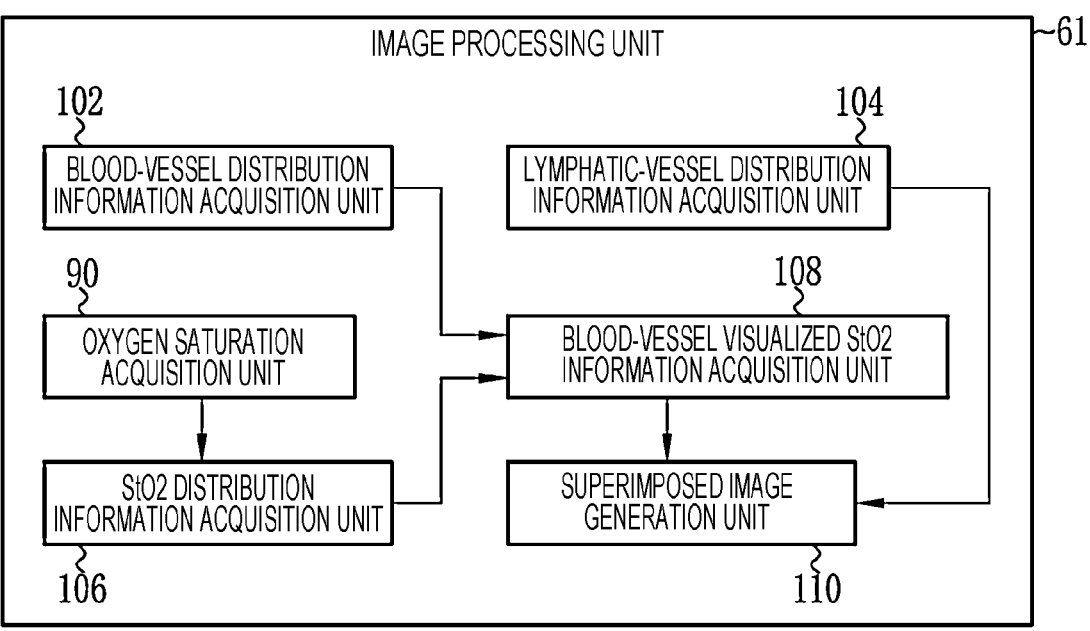
Figure 16:
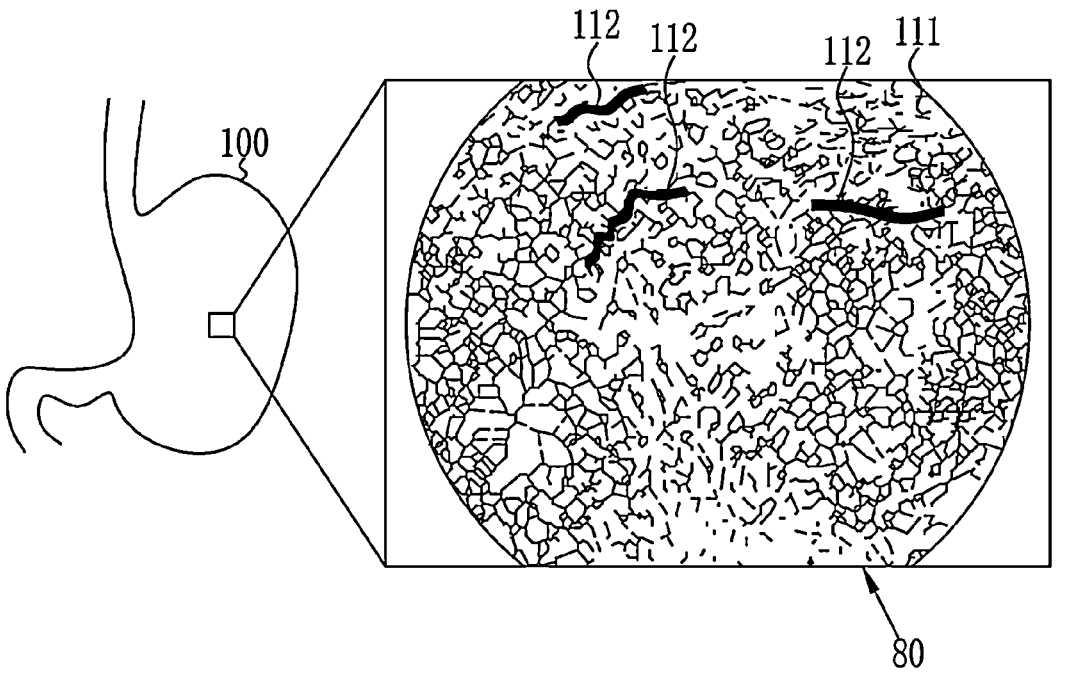
Figure 17:
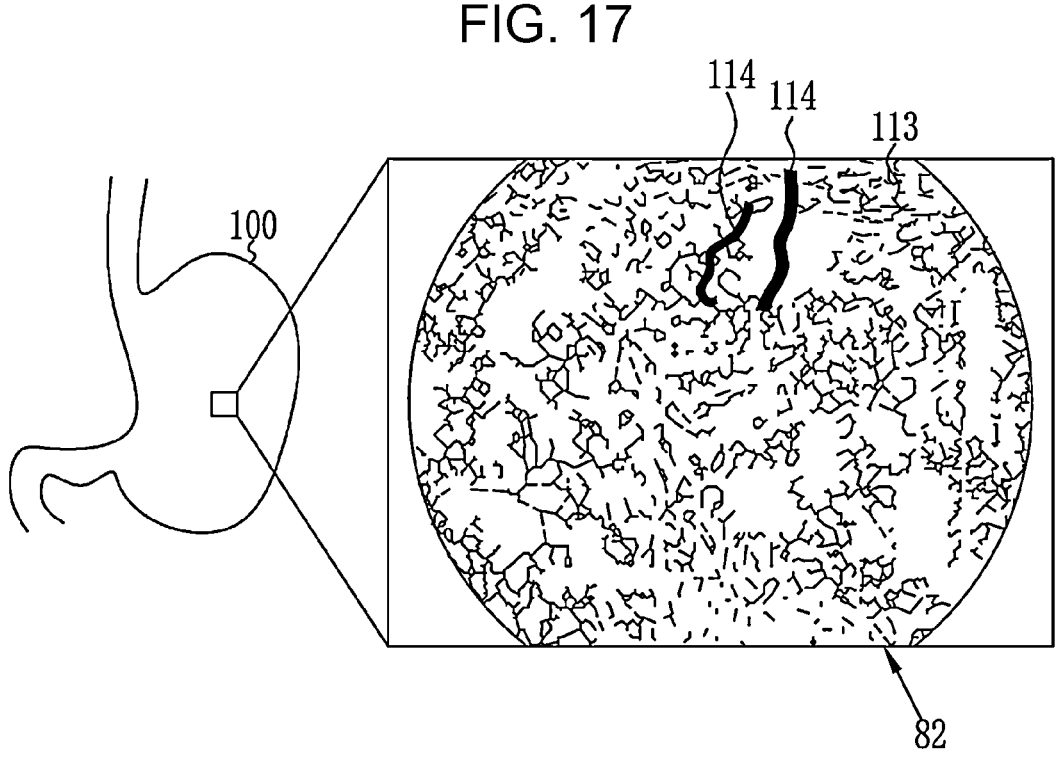
Figure 18:
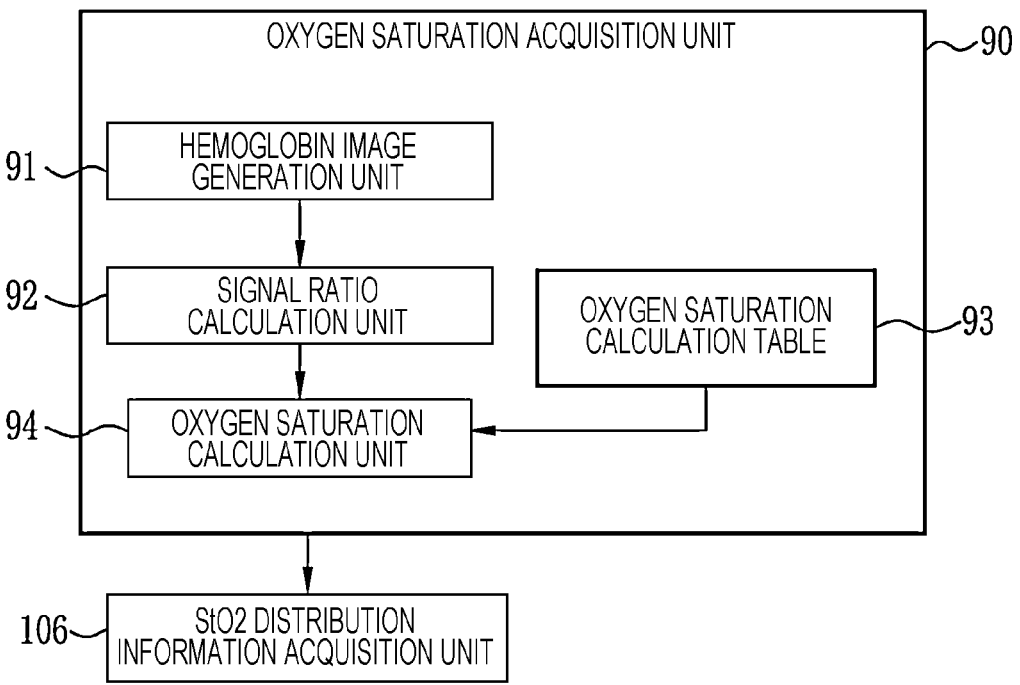
Figure 19:
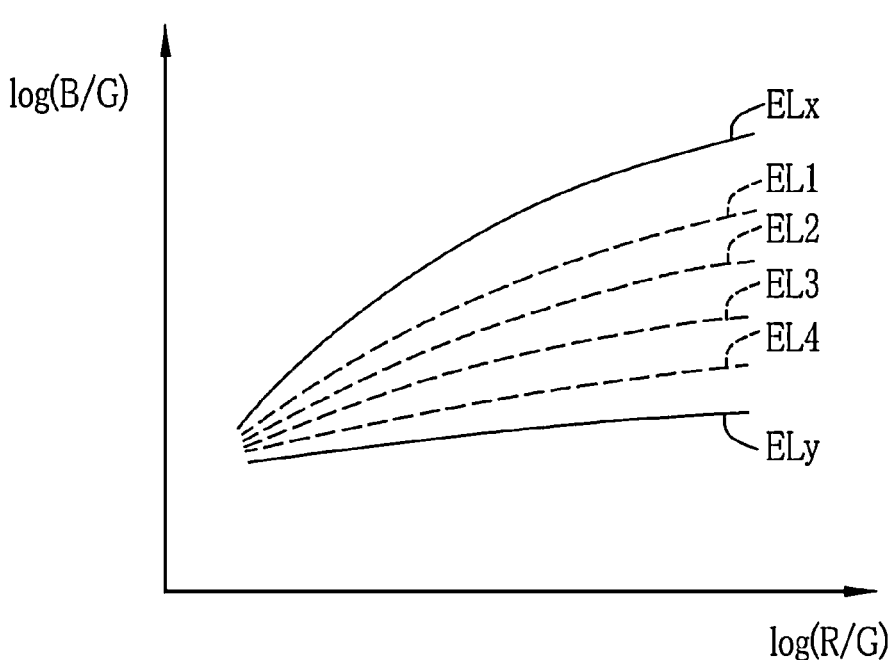
Figure 20:
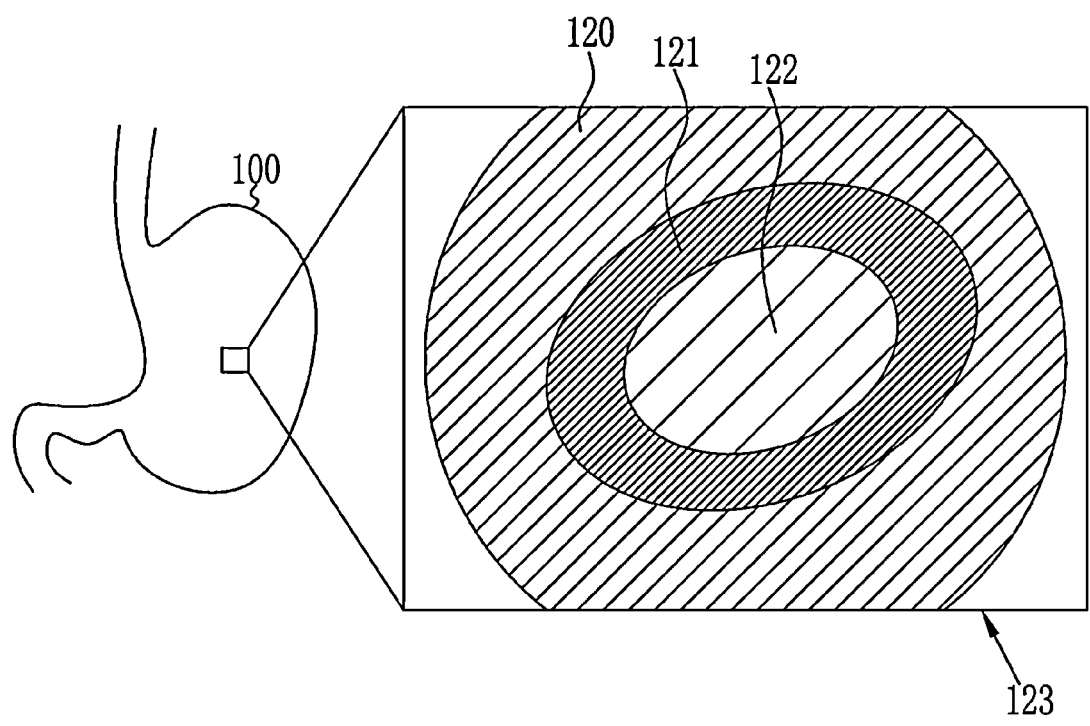
Figure 23:
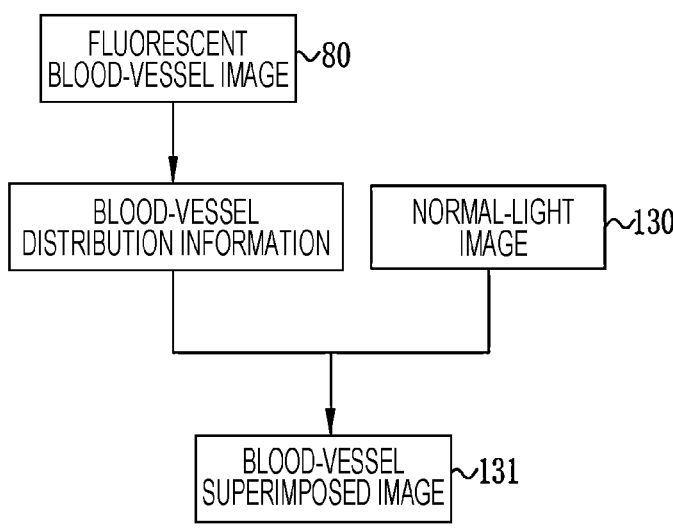
Figure 24:
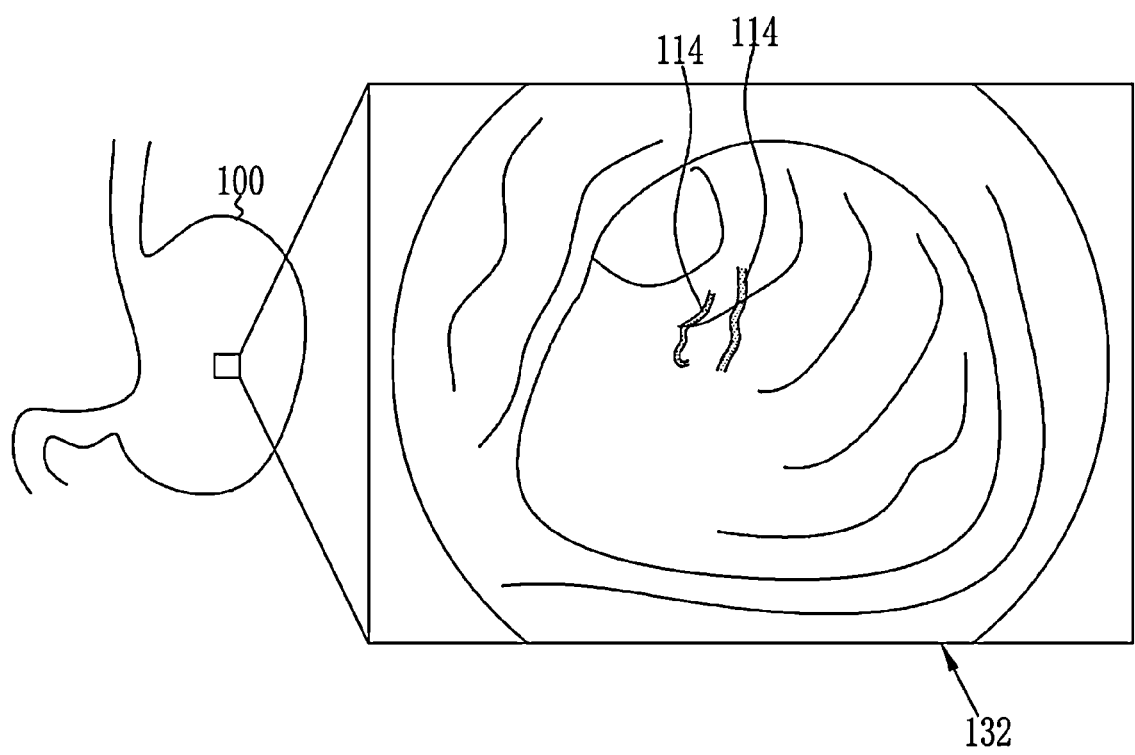
Figures 25, 26:
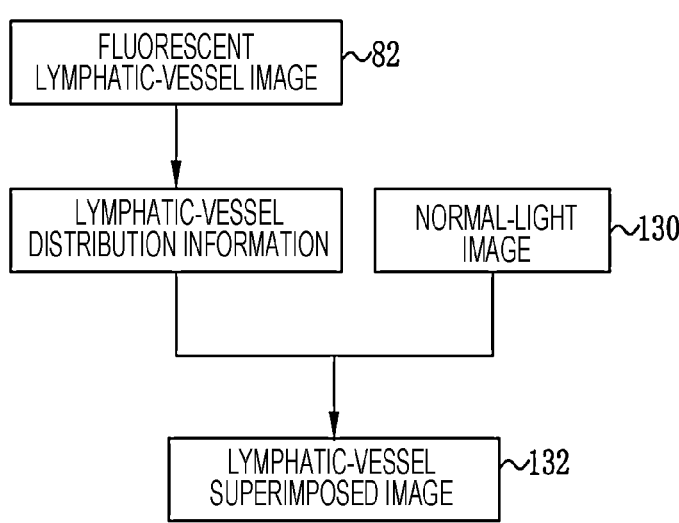
Figure 27:
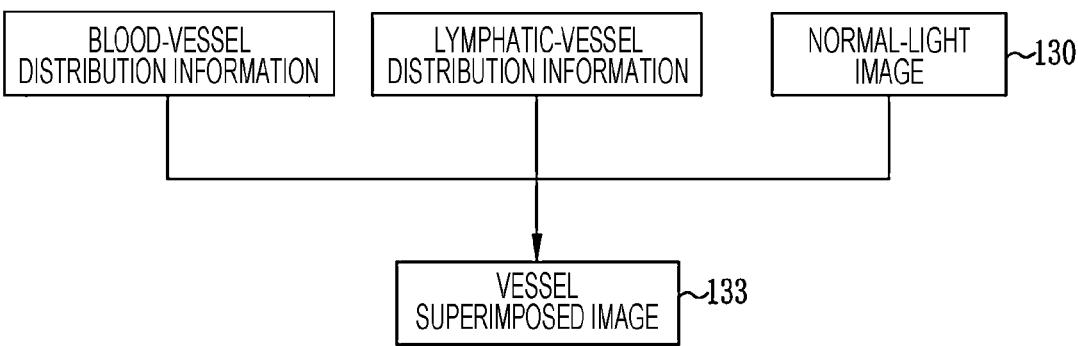
Figure 28:
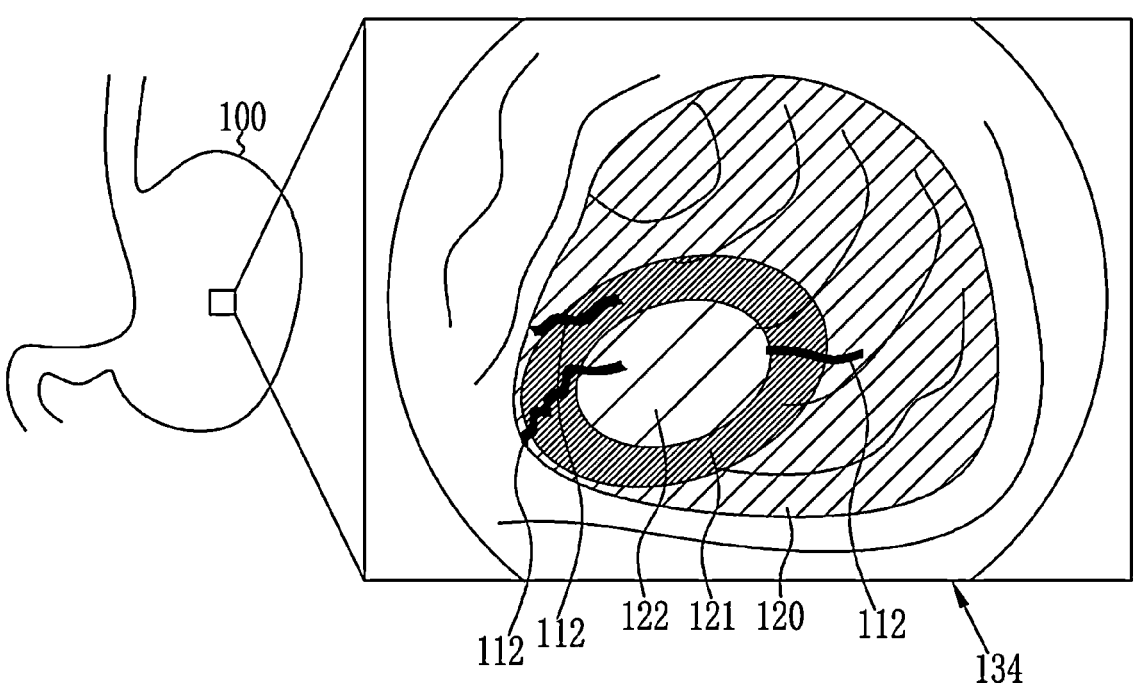
Figure 29:
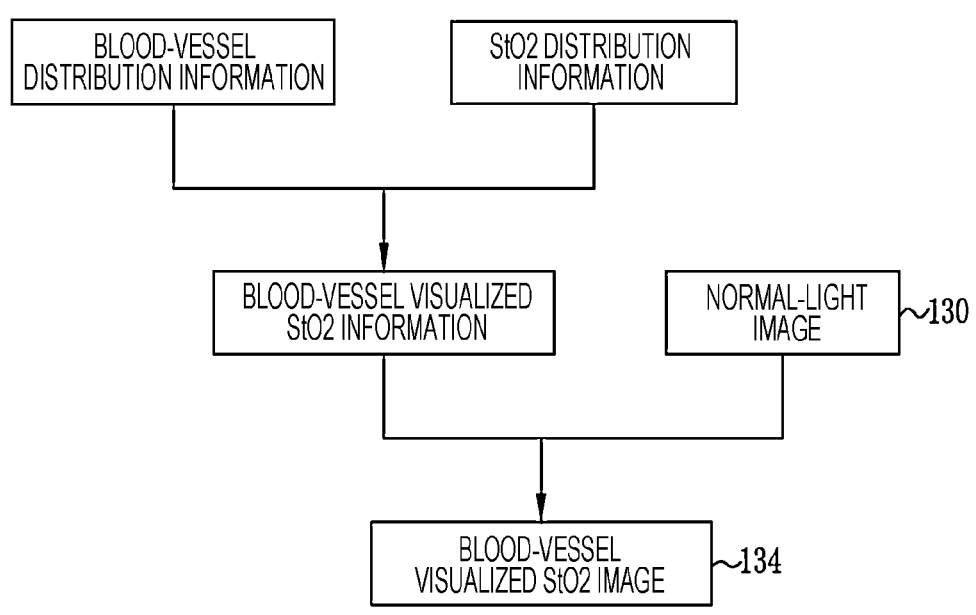
Figure 30:
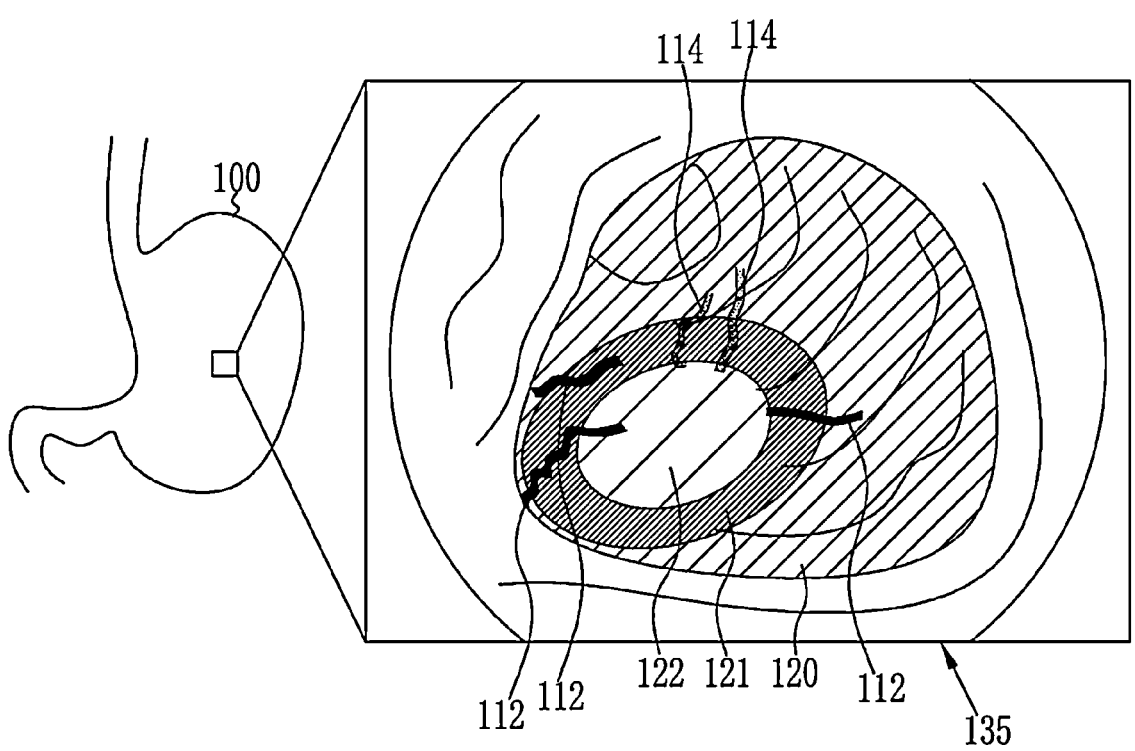
Figure 31:
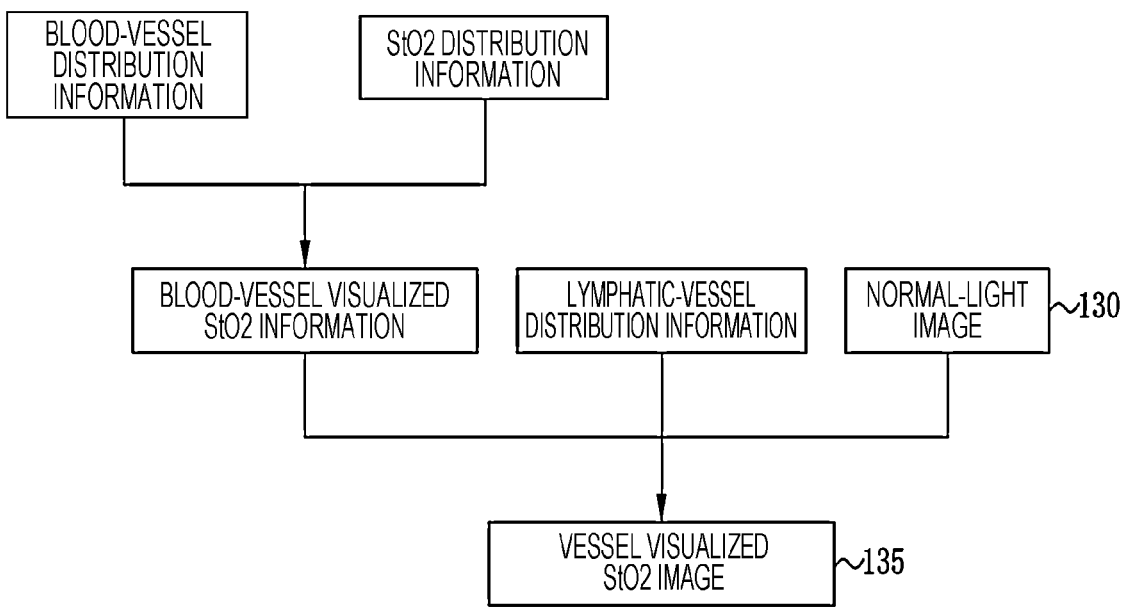
Figure 32:
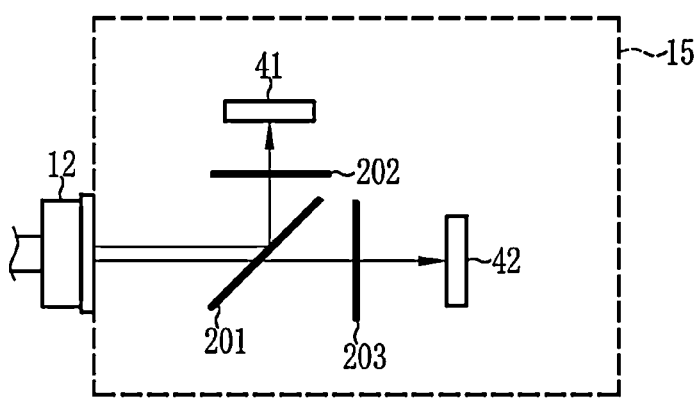
Figure 33:
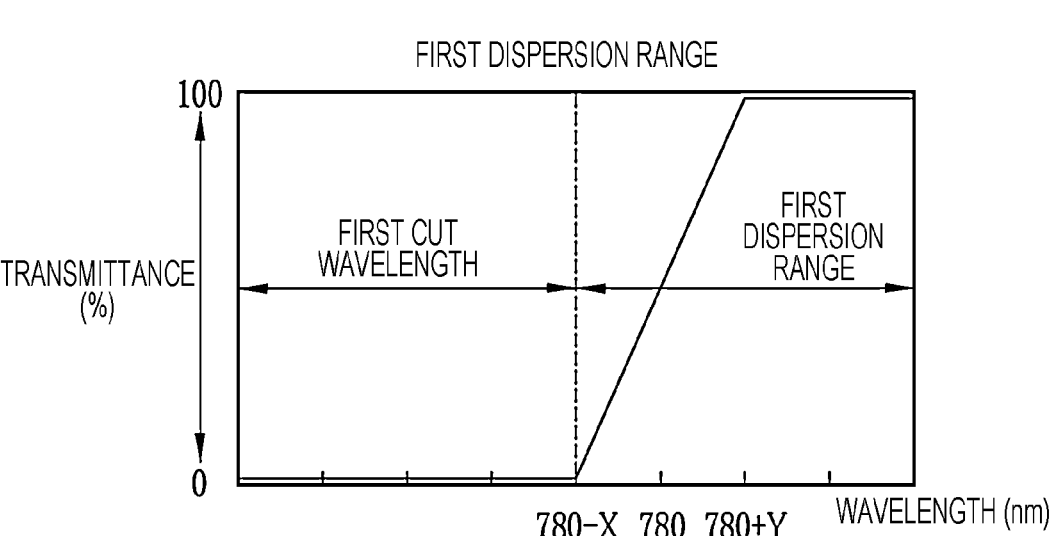
Figure 34:
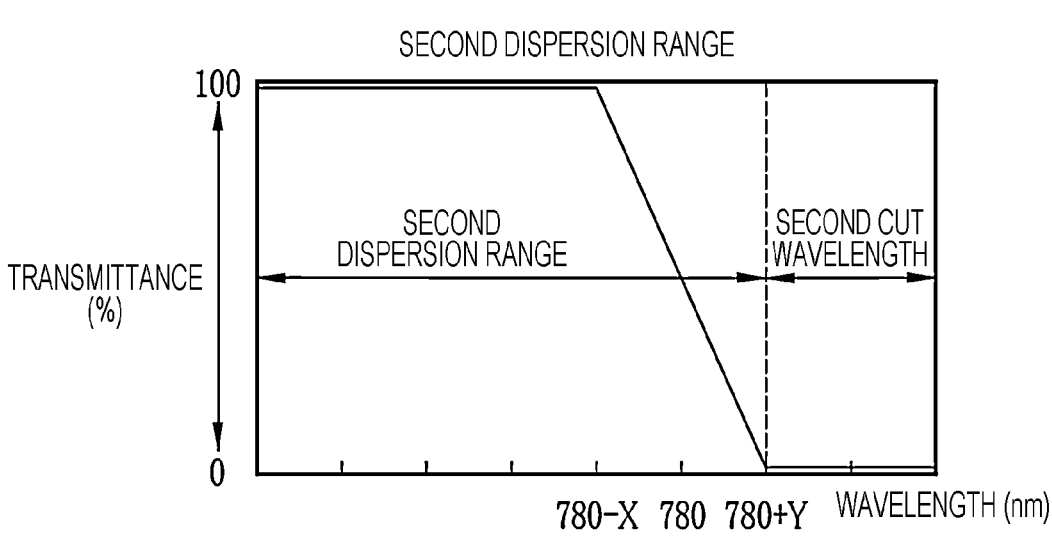
Figure 35:
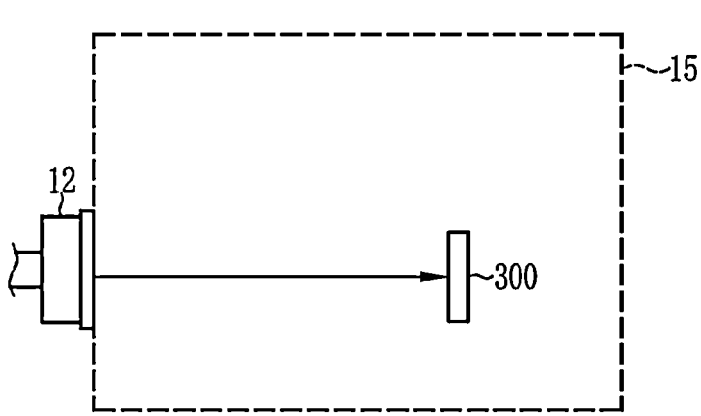
Figure 36:
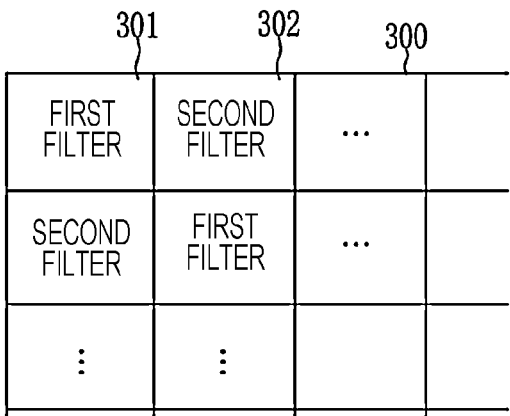

FIG. 15 is a block diagram illustrating functions of an image processing unit;

FIG. 16 illustrates a fluorescent blood-vessel image;

FIG. 17 illustrates a fluorescent lymphatic-vessel image;

FIG. 18 is a block diagram illustrating an oxygen saturation acquisition unit and an StO2 distribution information acquisition unit;

FIG. 19 is a graph for oxygen saturation calculation;

FIG. 20 illustrates an StO2 distribution image;

FIG. 21 is an explanatory diagram illustrating a relationship among a hemoglobin image, oxygen saturation, StO2 distribution information, and an StO2 distribution image;

FIG. 22 illustrates a blood-vessel superimposed image;

FIG. 23 is an explanatory diagram illustrating a relationship among a fluorescent blood-vessel image, blood-vessel distribution information, and a blood-vessel superimposed image;

FIG. 24 illustrates a lymphatic-vessel superimposed image;

FIG. 25 is an explanatory diagram illustrating a relationship among a fluorescent lymphatic-vessel image, lymphatic-vessel distribution information, and a lymphatic-vessel superimposed image;

FIG. 26 illustrates a vessel superimposed image;

FIG. 27 is an explanatory diagram illustrating a relationship among blood-vessel distribution information, lymphatic-vessel distribution information, and a vessel superimposed image;

FIG. 28 illustrates a blood-vessel visualized StO2 image;

FIG. 29 is an explanatory diagram illustrating a relationship among blood-vessel distribution information, StO2 distribution information, blood-vessel visualized StO2 information, and a blood-vessel visualized StO2 image;

FIG. 30 illustrates a vessel visualized StO2 image;

FIG. 31 is an explanatory diagram illustrating a relationship among blood-vessel distribution information, StO2 distribution information, blood-vessel visualized StO2 information, lymphatic-vessel distribution information, and a vessel visualized StO2 image;

FIG. 32 illustrates a configuration of a light receiving section in a second embodiment;

FIG. 33 is a graph illustrating a first dispersion range;

FIG. 34 is a graph illustrating a second dispersion range;

FIG. 35 illustrates a configuration of a light receiving section in a third embodiment; and FIG. 36 illustrates a configuration of a sensor in the third embodiment.

DESCRIPTION OF THE PREFERRED EMBODIMENTS

First Embodiment

Figures 1, 2:
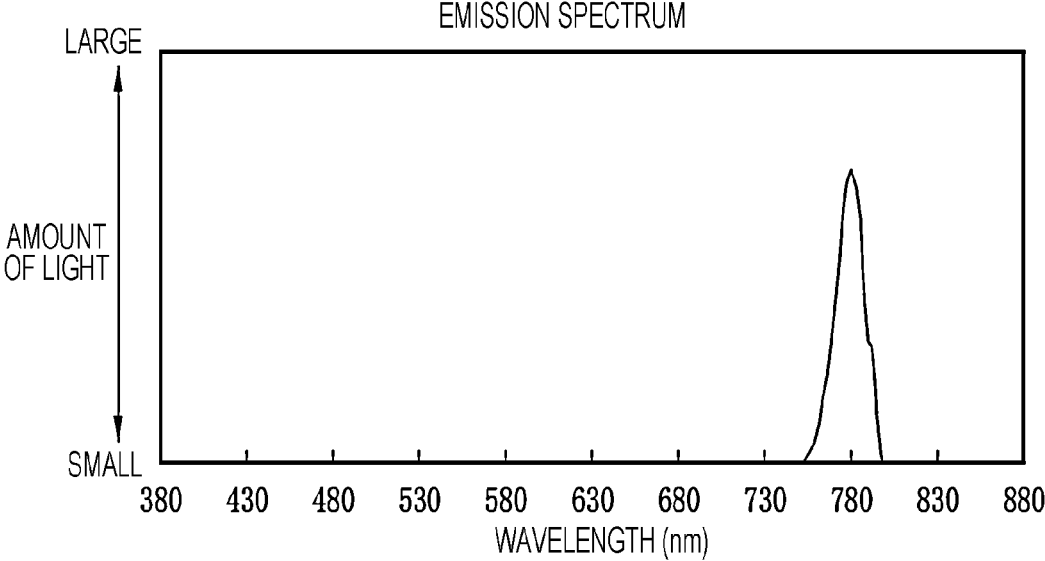
FIG. 1 illustrates a configuration of an endoscope system.
FIG. 2 is a graph illustrating a spectrum of a first wavelength range.

As illustrated in FIG. 1, an endoscope system 10 includes an endoscope 12, a light source device 14, a light receiving section 15, a processor device 16, a display 18, and a console 19.

The endoscope 12 is inserted into a subject. An optical system for forming a subject image and an optical system for irradiating the subject with illumination light are provided inside the endoscope 12. The light source device 14 generates the illumination light. The light receiving section 15 captures an image of the subject. The processor device 16 performs system control, image processing, and the like for the endoscope system 10. The display 18 is a display unit that displays an image captured by the endoscope 12. The console 19 is an input device used for inputting settings to the processor device 16, for example.

The light source device 14 includes a light source unit 20 that emits the illumination light and a light source control unit 22 that controls the operation of the light source unit 20.

The light source unit 20 emits the illumination light to illuminate the subject, excitation light to be used for emitting the illumination light, or the like. The light source unit 20 includes, for example, a light source such as a laser diode, an LED (Light Emitting Diode), a xenon lamp, or a halogen lamp, and at least emits the illumination light (normal light) of white color, light in a first wavelength range, or light in a second wavelength range. The white color includes so-called pseudo white, which is substantially the same as white in capturing an image of the subject by using the endoscope 12.

The light source unit 20 includes, for example, an optical filter that adjusts the wavelength range, spectrum, light amount, or the like of the illumination light or the excitation light, as necessary.

In the present embodiment, the light source unit 20 emits illumination light including the first wavelength range. Light in the first wavelength range is, for example, near-infrared light having a central wavelength of about 780 nm as illustrated in FIG. 2. The first wavelength range is a wavelength range of excitation light for exciting a fluorescent substance.

Figure 3:
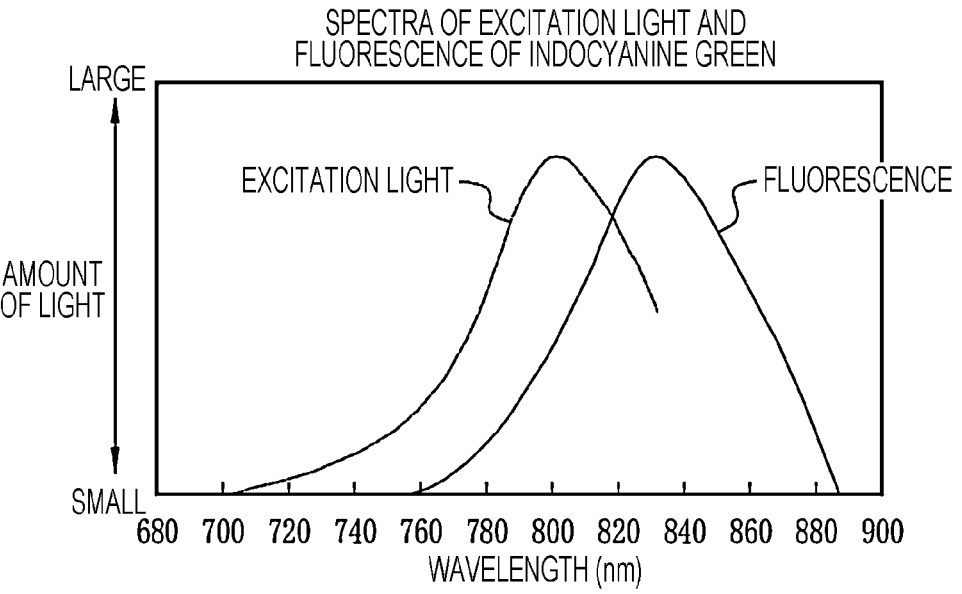
FIG. 3 is a graph illustrating spectra of excitation light and fluorescence of ICG.
Figure 4:
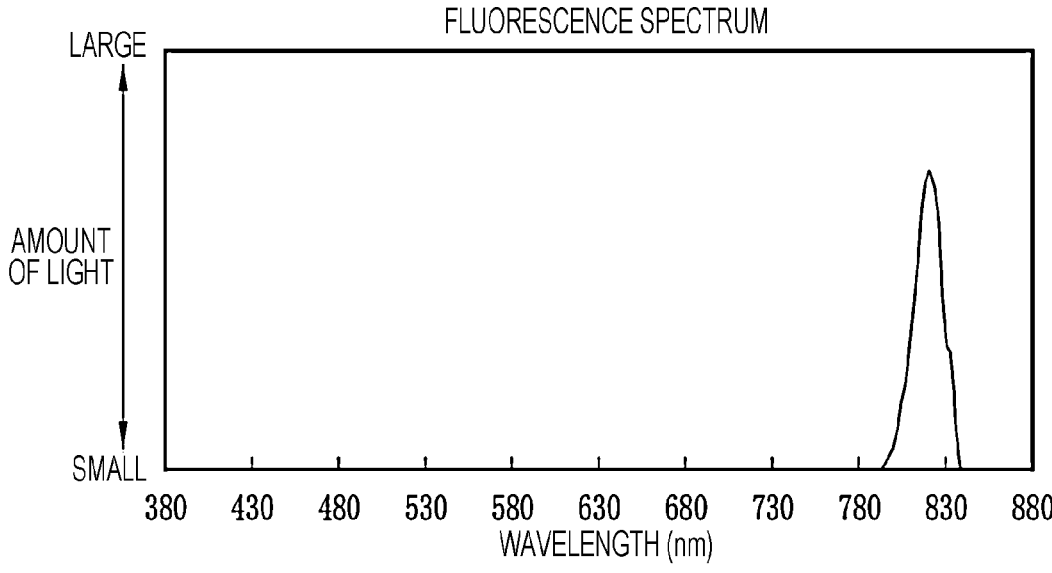
FIG. 4 is a graph illustrating a spectrum of a second wavelength range.

As illustrated in FIG. 3, the fluorescent substance emits fluorescence upon receiving the excitation light. Examples of the fluorescent substance include indocyanine green. Indocyanine green receives the excitation light, which is light in the first wavelength range, and emits fluorescence, which is light including a wavelength of the second wavelength range having a center wavelength different from that of the first wavelength range, as illustrated in FIG. 4.

Figure 5:
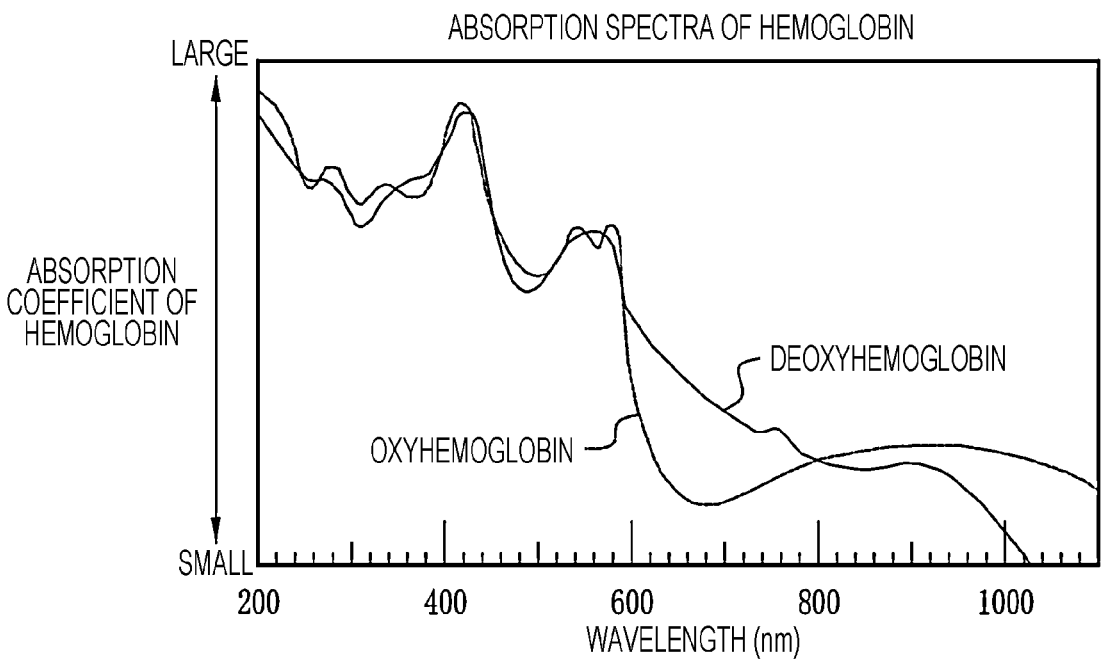
FIG. 5 is a graph illustrating an absorption coefficient of hemoglobin.

Furthermore, the first wavelength range is also a wavelength of light necessary for generating an image (hemoglobin image) indicating a distribution of hemoglobin included in the subject. As illustrated in FIG. 5, the central wavelength of about 780 nm is a wavelength at which the absorption coefficients of oxyhemoglobin and deoxyhemoglobin differ from each other. An image of the subject is captured by irradiating the subject with the illumination light including the light having a central wavelength of about 780 nm, and an StO2 (Tissue Oxygen Saturation) is calculated based on a difference between the absorption coefficients of oxyhemoglobin and deoxyhemoglobin included in the subject. Hereinafter, the tissue oxygen saturation is referred to as "StO2" or simply as "oxygen saturation".

That is, in the present invention, illumination light including a specific wavelength range (the first wavelength range) functions as the excitation light in the fluorescent substance and further as light for measuring oxygen saturation.

The light source control unit 22 controls turning on or turning off of the respective light sources that constitute the light source unit 20, light emission amounts thereof, and the like. The illumination light emitted by the light source unit 20 enters the endoscope 12 via a light guide 24, is guided to a distal end of the endoscope 12 via an optical system (an optical system for irradiating the subject with the illumination light) incorporated in the endoscope 12, and is emitted from the distal end of the endoscope 12 toward the subject. Subsequently, the subject is irradiated with the illumination light, and reflected light from the subject is guided to the light receiving section 15 via an optical system (an optical system for forming a subject image) incorporated in the endoscope 12.

The reflected light from the subject includes at least the light in the first wavelength range and the light in the second wavelength range, which is a wavelength range different from the first wavelength range.

Figure 6:
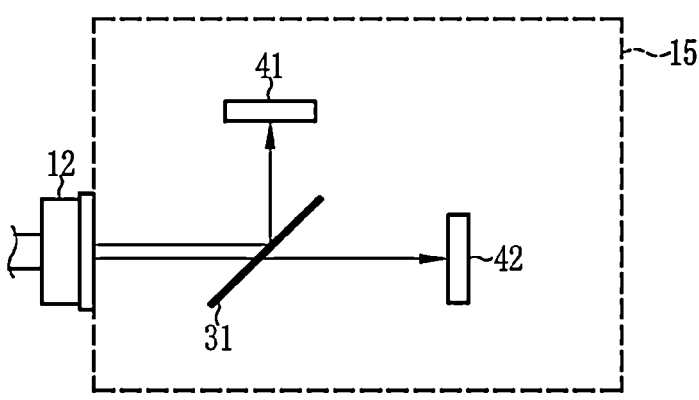
FIG. 6 illustrates a configuration of a light receiving section in a first embodiment.

In the first embodiment, as illustrated in FIG. 6, the light receiving section 15 that receives the reflected light from the subject and transmits an image signal includes a first spectral element 31, a first imaging element 41, and a second imaging element 42. Based on image signals sensed by the first imaging element 41 and the second imaging element 42, examination images such as a fluorescent blood-vessel image 80, a fluorescent lymphatic-vessel image 82, and a hemoglobin image, which will be described later, are generated.

The first spectral element 31 is a spectral element, such as a dichroic filter, a dichroic mirror, a beam splitter, or a half mirror, that reflects light in a specific wavelength range or higher and transmits light in a wavelength range lower than the specific wavelength range. Each of the first imaging element and the second imaging element is a CMOS (Complementary Metal Oxide Semiconductor) sensor or a CCD (Charge-Coupled Device) sensor.

Here, a combination of the first spectral element 31 and the first imaging element 41 is referred to as a first channel, and a combination of the first spectral element 31 and the second imaging element 42 is referred to as a second channel.

The first channel has a first sensing range. The first sensing range is a wavelength range that does not overlap with the first wavelength range or overlaps with the first wavelength range up to a half wavelength. The second channel has a second sensing range. The second sensing range is a wavelength range that does not overlap with the second wavelength range or overlaps with the second wavelength range up to a half wavelength. The half wavelength refers to a wavelength at which the sensitivity of the sensor is half the peak value.

The first spectral element 31 spectrally divides the reflected light from the subject into light in a wavelength range of the first spectral range and light in a wavelength range of the second spectral range at a specific wavelength. The light in the first spectral range is reflected by the first spectral element 31, and the light in the second spectral range is transmitted.

Figures 7, 8:
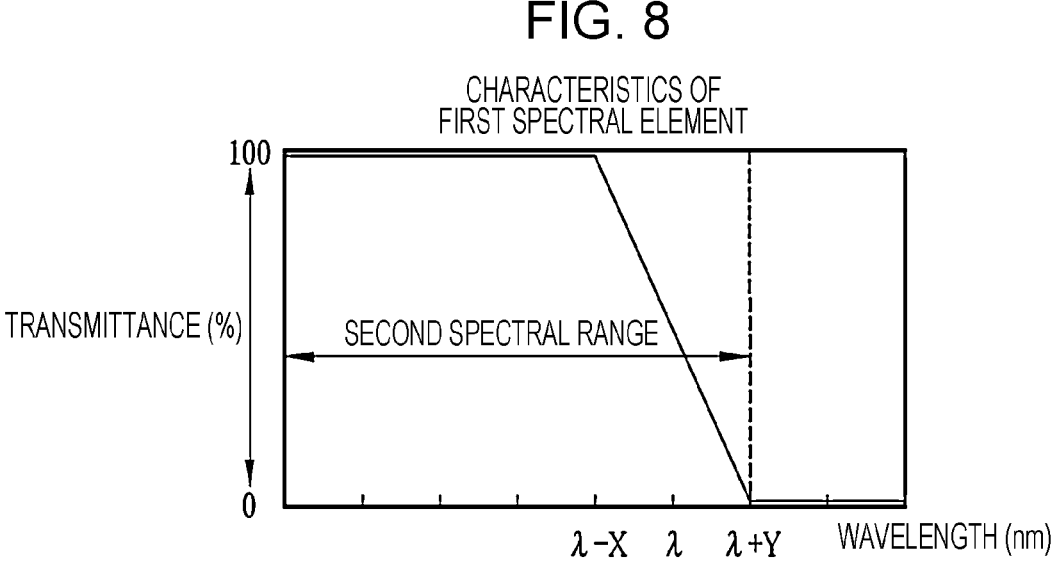
FIG. 7 is a graph illustrating characteristics of a first spectral element.
FIG. 8 is a graph illustrating characteristics of the first spectral element.

Specifically, as illustrated in FIG. 7, the reflectance of the first spectral element 31 increases at (λ–X) nm or more, and becomes maximum at (λ+Y) nm. On the other hand, as illustrated in FIG. 8, the transmittance of the first spectral element 31 decreases at (λ–X) nm or more, and becomes minimum at (λ+Y) nm. That is, the first spectral element 31 reflects light having a wavelength longer than (λ+Y) nm almost completely, sets light in a wavelength range longer than (λ–X) nm as the first spectral range, and transmits light in a wavelength range shorter than (λ+Y) nm as the second spectral range. Note that the values of λ, X, and Y vary depending on the first spectral element to be selected.

Figures 9, 10:
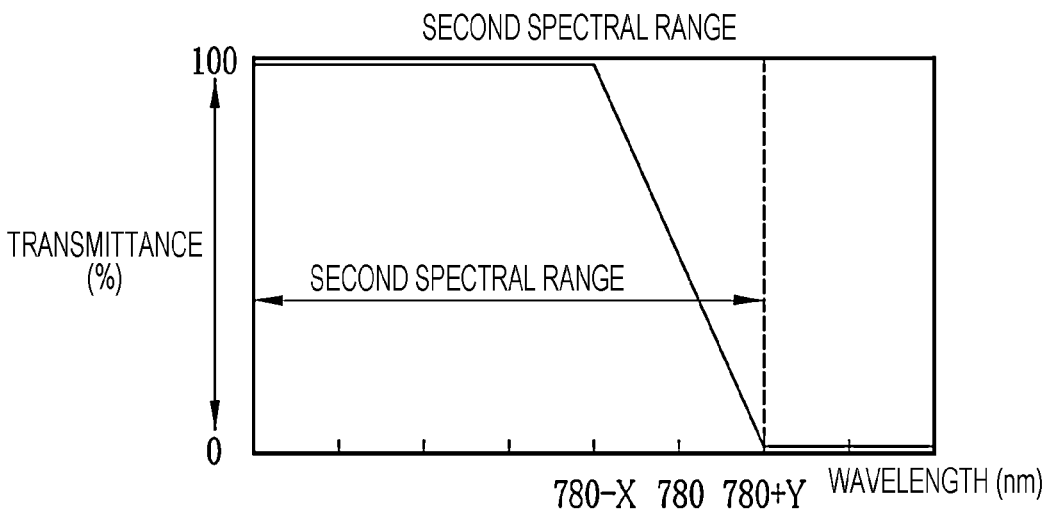
FIG. 9 is a graph illustrating an example of a first spectral range.
FIG. 10 is a graph illustrating an example of a second spectral range.

To give a specific numerical value, as illustrated in FIG. 9, light in the second wavelength range (e.g., fluorescence having a central wavelength of about 820 nm) is reflected by the first spectral element and becomes light in the first spectral range. As a specific numerical example of the wavelength range, as illustrated in FIG. 9, the reflectance increases at λ=(780–X) nm, becomes maximum at λ=(780+Y) nm, and becomes light in the first spectral range. The values of X and Y vary depending on the first spectral element to be selected.

On the other hand, as illustrated in FIG. 10, light in the first wavelength range (e.g., excitation light having a central wavelength of about 780 nm for measuring oxygen saturation) is transmitted through the first spectral element and becomes light in the second spectral range. As a specific numerical example of the wavelength range, as illustrated in FIG. 10, the transmittance decreases at λ=(780–X) nm, becomes minimum at λ=(780+X) nm, and becomes light in the second spectral range. The values of X and Y vary depending on the first spectral element to be selected.

The light in the first spectral range reflected by the first spectral element 31 enters the first imaging element 41. The light in the first spectral range forms an image on an imaging surface of the first imaging element 41. On the other hand, the light in the second spectral range transmitted through the first spectral element 31 enters the second imaging element 42. The light in the second spectral range forms an image on an imaging surface of the second imaging element 42.

The first imaging element 41 has a first transmission range. Specifically, the first imaging element 41 is a monochrome image sensor that is not provided with a color filter (e.g., Bayer filter), and can recognize light in the wavelength range illustrated in FIG. 11.

Figure 12:
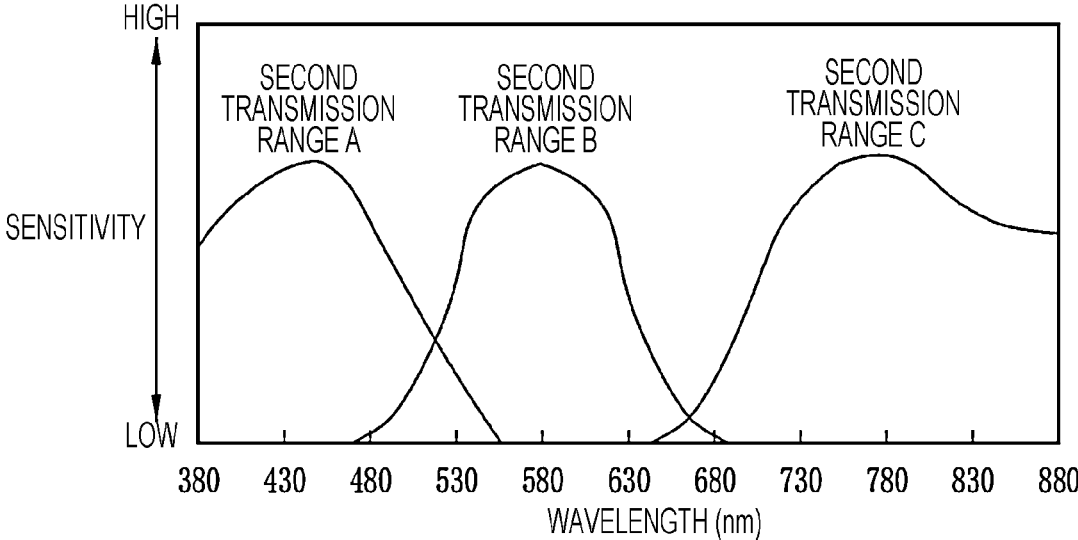
FIG. 12 is a graph illustrating a second transmission range A, a second transmission range B, and a second transmission range C.

The second imaging element 42 has a second transmission range. Specifically, the second imaging element 42 is a color image sensor that is provided with a color filter (e.g., Bayer filter). As illustrated in FIG. 12, the second transmission range is divided into a second transmission range A, a second transmission range B, and a second transmission range C, which are different from each other. For example, the second transmission range A corresponds to a blue wavelength range, the second transmission range B corresponds to a green wavelength range, and the second transmission range C corresponds to a red wavelength range.

Figures 13, 14:
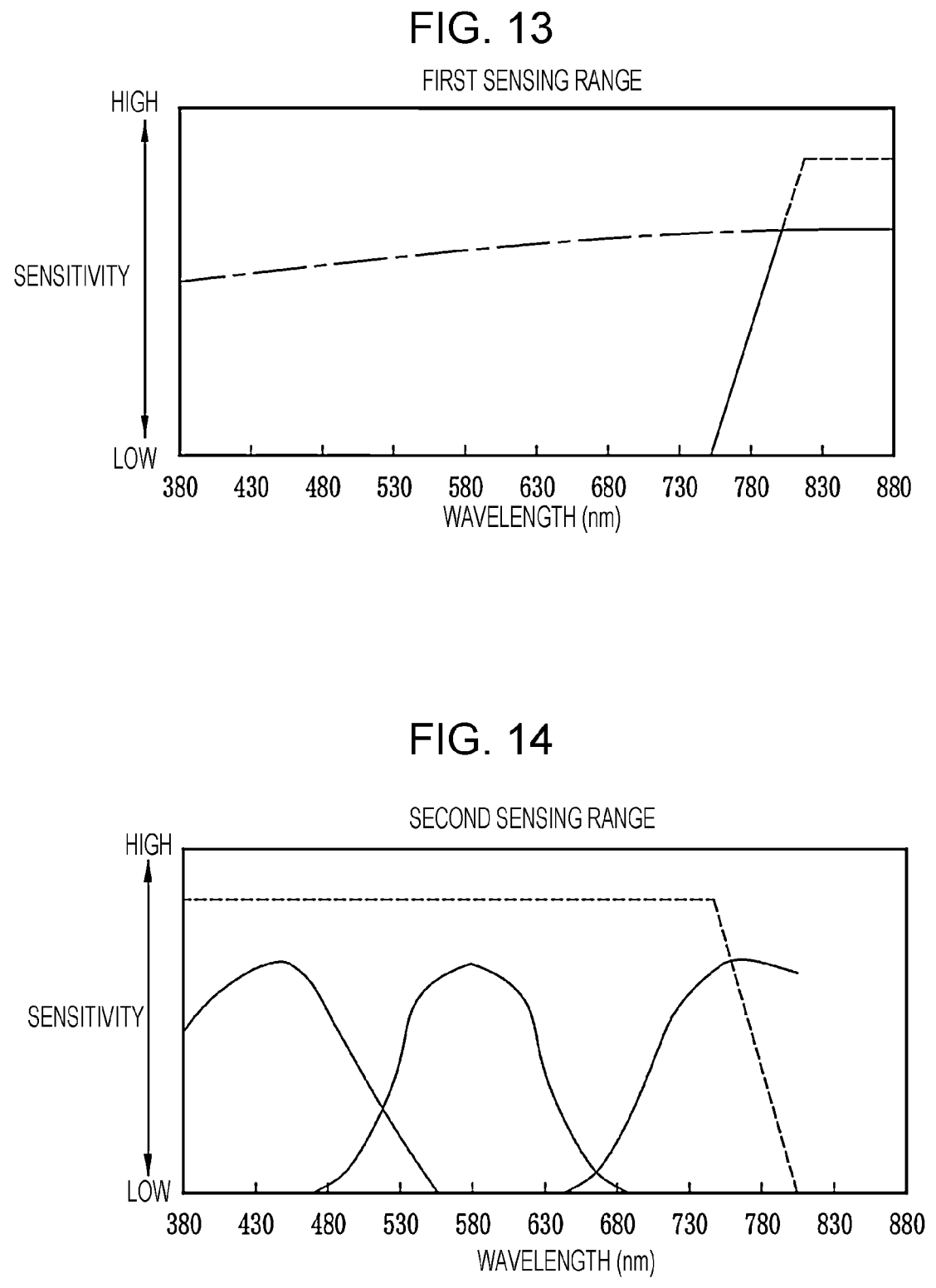

The first sensing range of the first channel is a wavelength range of a portion where the first spectral range and the first transmission range overlap each other and, in FIG. 13, corresponds to the solid line portion where the first spectral range indicated by the dotted line and the first transmission range indicated by the chain line overlap each other. The first imaging element 41 converts sensed light into a monochrome image signal.

The second sensing range of the second channel is a wavelength range of a portion where the second spectral range and the second transmission range overlap with each other and, in FIG. 14, corresponds to the solid line portion where the second spectral range indicated by the dotted line overlaps the second transmission range A, the second transmission range B, and the second transmission range C. The second imaging element 42 converts sensed light into a color image signal. Note that the color sensor used as the second imaging element 42 may convert the sensed light into a CMY signal instead of an RBG signal.

In the present embodiment, light having a central wavelength of about 780 nm, which is light in a wavelength range of the excitation light of the fluorescent substance and a wavelength range of light necessary for obtaining a hemoglobin image, is set as light in the first wavelength range and is used as the illumination light. In this case, the reflected light includes light in the first wavelength range and having a central wavelength of about 780 nm, which is reflected light from a living body, and light in the second wavelength range and having a central wavelength of about 820 nm, which is fluorescence from the fluorescent substance.

With the above-described configuration, by causing the first imaging element to sense light in the first spectral range and causing the second imaging element to sense light in the second spectral range, it is possible to obtain a fluorescence image and a hemoglobin image at a time using light in one specific wavelength range without using special excitation light illumination or illumination for measuring oxygen saturation.

The image signals transmitted from the first imaging element 41 and the second imaging element 42 are transmitted to an image processing unit 61 of the processor device 16. The processor device 16 includes a control unit 59, the image processing unit 61, and a display control unit 66. In the processor device 16, the functions of the image processing unit 61 and the display control unit 66 are implemented by a program in a program memory being operated by the control unit 59 configured by an image control processor. The functions of the image processing unit 61 and the display control unit 66 will be described later.

Now, the function of the image processing unit 61 will be described below with reference to FIG. 15.

The image signal converted from the light in the first sensing range by the first imaging element 41 is transmitted to a blood-vessel distribution information acquisition unit 102 and/or a lymphatic-vessel distribution information acquisition unit 104 in the image processing unit 61. The blood-vessel distribution information acquisition unit 102 generates the fluorescent blood-vessel image 80 as illustrated in FIG. 16 based on the image signal received from the first imaging element 41. In the fluorescent blood-vessel image 80, the localization of indocyanine green is visualized as relatively thin blood vessels 111, such as arterioles, venules, and capillaries, and relatively thick blood vessels 112. The blood-vessel distribution information acquisition unit 102 acquires blood-vessel distribution information from the generated fluorescent blood-vessel image 80.

The lymphatic-vessel distribution information acquisition unit 104 generates the fluorescent lymphatic-vessel image 82 as illustrated in FIG. 17 based on the image signal received from the first imaging element 41. In the fluorescent lymphatic-vessel image 82, the localization of indocyanine green is visualized as relatively thin lymphatic vessels 113 and relatively thick lymphatic vessels 114. The lymphatic-vessel distribution information acquisition unit 104 acquires lymphatic-vessel distribution information from the generated fluorescent lymphatic-vessel image 82. Note that FIGS. 16 and 17 each illustrate an enlarged captured image of a part of a stomach 100 as a subject.

Whether to generate one or both of the fluorescent blood-vessel image 80 and the fluorescent lymphatic-vessel image 82 is set by a user before or during an examination. This is because a user such as a doctor determines whether to perform imaging of blood vessels, imaging of lymphatic vessels, or imaging of both for an examinee. When a user performs fluorescence imaging using a fluorescent substance, the fluorescent substance is administered to a vein or a lymph node. When the fluorescent substance is administered into a vein of the examinee, fluorescence imaging of blood vessels is performed. On the other hand, when the fluorescent substance is administered into a lymph node of the examinee, fluorescence imaging of lymphatic vessels is performed. Note that the image processing unit 61 may automatically determine blood vessels or lymphatic vessels from, for example, the distribution of the fluorescent substance obtained from the fluorescent blood-vessel image 80 or the fluorescent lymphatic-vessel image 82 without setting whether the transmission destination of the image signal converted by the first imaging element 41 is the blood-vessel distribution information acquisition unit 102 and/or the lymphatic-vessel distribution information acquisition unit 104.

The blood-vessel distribution information is a feature amount of blood vessels obtained from the fluorescent blood-vessel image 80. A feature amount related to the fluorescent blood-vessel image 80 is preferably classified based on whether an observation target is located in at least one of a surface layer, a middle layer, or a deep layer. The feature amount is preferably a value obtained from the shape, pixel density, or the like of the observation target. Examples of items of the feature amount include a blood vessel density, the shape of a blood vessel, the number of branches of a blood vessel, the thickness of a blood vessel, the length of a blood vessel, the degree of meandering of a blood vessel, the degree of invasion of a blood vessel, and the degree of irregularity of a blood vessel. The feature amount is preferably at least one of these values or a value obtained by combining two or more of these values. Note that the items of the feature amount are not limited to these, and may be appropriately added according to the use situation.

The lymphatic-vessel distribution information is a feature amount of lymphatic vessels obtained from the fluorescent lymphatic-vessel image 82. The feature amount is preferably a value obtained from the shape, pixel density, or the like of the observation target. Examples of items of the feature amount include a lymphatic vessel density, the shape of a lymphatic vessel, the number of branches of a lymphatic vessel, the thickness of a lymphatic vessel, the length of a lymphatic vessel, the degree of meandering of a lymphatic vessel, the degree of invasion of a lymphatic vessel, and the degree of irregularity of a lymphatic vessel. The feature amount is preferably at least one of these values or a value obtained by combining two or more of these values. Note that the items of the feature amount are not limited to these, and may be appropriately added according to the use situation.

With the above-described configuration, it is possible to visualize, from the blood-vessel distribution information and/or the lymphatic-vessel distribution information, a location where blood flow failure occurs, a blood flow concentration, and how (normally/irregularly) blood vessels and/or lymphatic vessels of what property (thickness/depth) are distributed.

The fluorescent blood-vessel image 80 acquired by the blood-vessel distribution information acquisition unit 102 may be transmitted to the display control unit 66. The fluorescent blood-vessel image 80 may also be transmitted to a superimposed image generation unit 110 described later. The fluorescent blood-vessel image 80 may also be transmitted to a blood-vessel visualized StO2 information acquisition unit 108 described later.

The fluorescent lymphatic-vessel image 82 acquired by the lymphatic-vessel distribution information acquisition unit 104 may be transmitted to the display control unit 66. The fluorescent lymphatic-vessel image 82 may also be transmitted to the superimposed image generation unit 110 described later. In addition, together with the fluorescent lymphatic-vessel image 82, the lymphatic-vessel distribution information may be transmitted to the superimposed image generation unit 110.

Now, an oxygen saturation acquisition unit 90 will be described below.

The image signal converted from the light in the second sensing range by the second imaging element 42 is transmitted to the oxygen saturation acquisition unit 90 in the image processing unit 61. A hemoglobin image generation unit 91 provided in the oxygen saturation acquisition unit 90 illustrated in FIG. 18 generates a hemoglobin image based on the image signal received from the second imaging element 42, and transmits image information to a signal ratio calculation unit 92. Information on the result calculated by the signal ratio calculation unit 92 and an oxygen saturation calculation table 93 is transmitted to an oxygen saturation calculation unit 94 to obtain the oxygen saturation.

Image processing for measuring oxygen saturation, performed by the oxygen saturation acquisition unit 90, is processing performed on an image signal obtained by emitting light including the wavelength range of the first wavelength range. The image signal received from the second imaging element may include a B image signal, a G image signal, and an R image signal based on light in the second transmission range A, the second transmission range B, and the second transmission range C. The signal ratio calculation unit 92 performs signal ratio calculation processing by calculating, for example, a first signal ratio (B/G) representing a ratio between the B image signal and the G image signal and a second signal ratio (R/G) representing a ratio between the R image signal and the G image signal, and transmits a signal ratio calculation processing result to the oxygen saturation calculation unit 94. The oxygen saturation calculation unit 94 calculates the oxygen saturation corresponding to the first signal ratio and the second signal ratio with reference to the signal ratio calculation processing result and the oxygen saturation calculation table 93.

The oxygen saturation calculation table 93 stores a correlation among the oxygen saturation, the first signal ratio, and the second signal ratio. Specifically, as illustrated in FIG. 19, a two-dimensional table is configured in which isopleths ELx, EL1, EL2, EL3, ELy, and the like of the oxygen saturations are defined in a two-dimensional space having the first signal ratio (B/G) and the second signal ratio (R/G) as axes. The isopleth ELx indicates that the oxygen saturation is "0%", the isopleth EL1 indicates that the oxygen saturation is "30%", the isopleth EL2 indicates that the oxygen saturation is "50%", and the isopleth EL3 indicates that the oxygen saturation is "80%". Note that the positions and shapes of the isopleths with respect to the first signal ratio (B/G) and the second signal ratio (R/G) are obtained in advance by physical simulation of light scattering. In addition, the first signal ratio (B/G) and the second signal ratio (R/G) are preferably in a log scale. The oxygen saturation is transmitted to an StO2 distribution information acquisition unit 106.

The StO2 distribution information acquisition unit 106 acquires StO2 distribution information from the oxygen saturation calculated by the oxygen saturation acquisition unit 90. The oxygen saturation is numerical information based on the distribution of oxyhemoglobin and deoxyhemoglobin, and the StO2 distribution information is obtained by applying the numerical information to a hemoglobin image, two-dimensionally mapping which portion is hypoxic in the hemoglobin image, and visualizing approximate positions of blood vessels. The StO2 distribution information is transmitted to the blood-vessel visualized StO2 information acquisition unit 108. In addition, an StO2 distribution image 123 as illustrated in FIG. 20 in which the StO2 distribution information is superimposed on the hemoglobin image may be generated and transmitted to the display control unit 66.

From the StO2 distribution image 123 illustrated in FIG. 20, a normal value region 120 in which the oxygen saturation is normal, a hyperoxic region 121 in which the oxygen saturation is high, and a hypoxic region 122 in which the oxygen saturation is low are visualized in different colors. The display of the StO2 distribution information is not limited to this, and the oxygen saturation may be displayed as a numerical value or the like. Note that FIG. 20 illustrates an enlarged captured image of a part of the stomach 100 as a subject.

The functions of the oxygen saturation acquisition unit 90 and the StO2 distribution information acquisition unit 106 are collectively illustrated in FIG. 21. Upon receiving the image signal, the oxygen saturation acquisition unit 90 generates the hemoglobin image, acquires the oxygen saturation, and transmits the oxygen saturation to the StO2 distribution information acquisition unit 106. The StO2 distribution information acquisition unit 106 acquires the StO2 distribution information. The StO2 distribution information acquisition unit 106 may generate the StO2 distribution image 123 illustrated in FIG. 20. The StO2 distribution information may also be transmitted to the blood-vessel visualized StO2 information acquisition unit 108 described later.

Now, the superimposed image generation unit 110 will be described below.

A normal-light image 130 based on the reflected light obtained by irradiating the subject with the normal light is transmitted to the superimposed image generation unit 110. The superimposed image generation unit 110 generates images as illustrated in FIGS. 22, 24, 26, 28, and 30 in which information described later is superimposed on the normal-light image 130.

The superimposed image generation unit 110 generates a blood-vessel superimposed image 131 as illustrated in FIG. 22 in which the blood-vessel distribution information is superimposed on the normal-light image 130. In the blood-vessel superimposed image 131, the shape, position, size, range, and the like of blood vessels are visualized on the normal-light image 130. In FIG. 22, only the thick blood vessels 112 are illustrated for simplicity. As the flow of images and information, as illustrated in FIG. 23, upon the blood-vessel distribution information acquisition unit 102 receiving an image signal, the fluorescent blood-vessel image 80 (see FIG. 16) is generated, and also, the blood-vessel distribution information is acquired and transmitted to the display control unit 66 or the superimposed image generation unit 110. The blood-vessel distribution information is superimposed on the normal-light image 130 to generate the blood-vessel superimposed image 131 illustrated in FIG. 22.

Furthermore, the superimposed image generation unit 110 generates a lymphatic-vessel superimposed image 132 as illustrated in FIG. 24 in which the lymphatic-vessel distribution information is superimposed on the normal-light image 130. In the lymphatic-vessel superimposed image 132, the shape, position, size, range, and the like of lymphatic vessels are visualized on the normal-light image 130. In FIG. 24, only the thick lymphatic vessels 114 are illustrated for simplicity. As the flow of images and information, as illustrated in FIG. 25, upon the lymphatic-vessel distribution information acquisition unit 104 receiving an image signal, the fluorescent lymphatic-vessel image 82 (see FIG. 17) is generated, and also, the lymphatic-vessel distribution information is acquired and transmitted to the display control unit 66 or the superimposed image generation unit 110. The lymphatic-vessel distribution information is superimposed on the normal-light image 130 to generate the lymphatic-vessel superimposed image 132 illustrated in FIG. 24.

In addition, the superimposed image generation unit 110 may receive the blood-vessel distribution information and the lymphatic-vessel distribution information and generate a vessel superimposed image 133 illustrated in FIG. 26. The flow of images and information is as illustrated in FIG. 27. The vessel is a generic term including a blood vessel and a lymph vessel.

Furthermore, the superimposed image generation unit 110 generates a blood-vessel visualized StO2 image 134 as illustrated in FIG. 28 by superimposing, on the normal-light image 130, blood-vessel visualized StO2 information obtained by combining the blood-vessel distribution information and the StO2 distribution information acquired by the blood-vessel visualized StO2 information acquisition unit 108 to increase the accuracy of the information on blood vessels.

The blood-vessel visualized StO2 information acquisition unit 108 receives the StO2 distribution information from the StO2 distribution information acquisition unit 106 and the blood-vessel distribution information from the blood-vessel distribution information acquisition unit 102, and acquires the blood-vessel visualized StO2 information. The blood-vessel visualized StO2 information is information obtained by combining information obtained by visualizing the oxygen saturation obtained from the StO2 distribution information and information about the property and three-dimensional distribution of blood vessels obtained from the blood-vessel distribution information, and can improve the accuracy of information necessary for determining the location, grade, infiltration range, or the like of a tumor. The blood-vessel visualized StO2 information is transmitted to the superimposed image generation unit 110.

In the blood-vessel visualized StO2 image 134 generated by the superimposed image generation unit 110, the blood-vessel visualized StO2 information is visualized on the normal-light image 130. For example, as illustrated in FIG. 28, the StO2 distribution information and the thick blood vessels 112 are illustrated, but the display method is not limited thereto. For example, the location, grade, infiltration range, or the like of an expected tumor may be indicated. As the flow of images and information, as illustrated in FIG. 29, the blood-vessel visualized StO2 information acquisition unit 108 receives the blood-vessel distribution information and the StO2 distribution information, and acquires the blood-vessel visualized StO2 information. The blood-vessel visualized StO2 information is transmitted to the superimposed image generation unit 110, and the blood-vessel visualized StO2 image 134 illustrated in FIG. 28 is generated.

The superimposed image generation unit 110 also generates a vessel visualized StO2 image 135 as illustrated in FIG. 30 in which the blood-vessel visualized StO2 information and the lymphatic-vessel distribution information are superimposed on the normal-light image 130. In the vessel visualized StO2 image 135, information obtained by combining the blood-vessel visualized StO2 information and the lymphatic-vessel distribution information is visualized on the normal-light image 130. For example, as illustrated in FIG. 30, the blood-vessel visualized StO2 information, the thick blood vessels 112, and the thick lymphatic vessels 114 are illustrated, but the display method is not limited thereto. Thin blood vessels and thin lymphatic vessels may be displayed, and the thickness of the vessels to be displayed can be set as appropriate. The flow of images and information for generating the vessel visualized StO2 image 135 is as illustrated in FIG. 31.

The blood-vessel superimposed image 131, the lymphatic-vessel superimposed image 132, the vessel superimposed image 133, the blood-vessel visualized StO2 image 134, and the vessel visualized StO2 image 135 generated by the superimposed image generation unit 110 are transmitted to the display control unit 66, and are output and displayed on the display 18.

Second Embodiment

In the first embodiment described above, an embodiment in which the light receiving section 15 has the first spectral element 31, the first imaging element 41, and the second imaging element 42 has been described. In contrast, in a second embodiment, the light receiving section 15 has a second spectral element 201, a first optical element 202, a second optical element 203, the first imaging element 41, and the second imaging element 42 (refer to FIG. 32).

In the present embodiment, a combination of the first optical element 202 and the first imaging element 41 is referred to as a first channel, and a combination of the second optical element 203 and the second imaging element 42 is referred to as a second channel.

The second spectral element 201 is a spectral element that spectrally divides a type of light having the same wavelength range into at least two or more types of light having the same wavelength range. Examples of the second spectral element 201 include a plate-type beam splitter, a cube-type beam splitter, and the like.

The first optical element 202 is an optical element that reflects or absorbs light in a wavelength range of a first cut wavelength included in the light spectrally divided by the second spectral element 201, and transmits light in a first dispersion range. The first cut wavelength preferably includes the wavelength range of the first wavelength range completely or up to the half wavelength. Examples of the first optical element 202 include a long-pass filter, a band-pass filter, and the like. Alternatively, the first optical element 202 may be formed by combining these elements.

Specifically, for example, as illustrated in FIG. 33, the first optical element 202 reflects or absorbs light less than the first cut wavelength $\lambda = (780-X)$ nm. The transmittance of the first optical element 202 increases in a wavelength range of $\lambda = (780-X)$ nm or more, and becomes maximum at $\lambda = (780+Y)$ nm. That is, the first dispersion range is a wavelength range of $\lambda = (780-X)$ nm or more from which light less than $\lambda = (780-X)$ nm is excluded. The wavelength range to be the first cut wavelength can be determined to any wavelength range, and the values of X and Y vary depending on the second spectral element to be selected.

Figure 11:
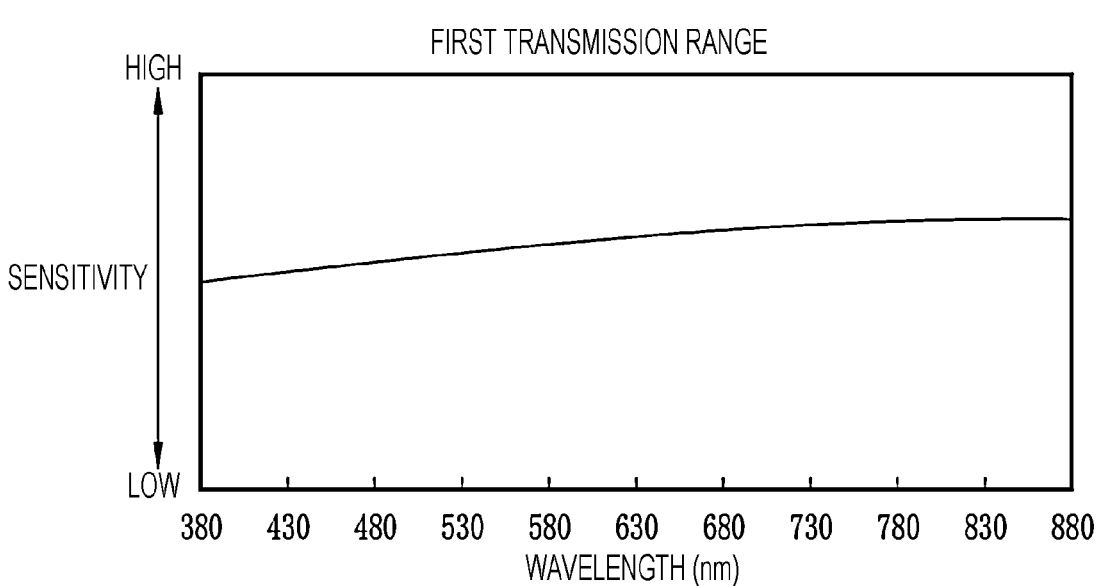
FIG. 11 is a graph illustrating a first transmission range.

As in the first embodiment, the first imaging element 41 is a monochrome image sensor having the first transmission range illustrated in FIG. 11. Light in the first dispersion range enters the first imaging element 41. The first sensing range, which is a wavelength range of light sensed by the first imaging element 41, is a wavelength range in which the first dispersion range and the first transmission range overlap each other. Specifically, the first sensing range is substantially the same as that in the first embodiment, and is the range indicated by the solid line in FIG. 13. In the present embodiment, the chain line in FIG. 13 corresponds to the first transmission range, and the dotted line corresponds to the first dispersion range.

The second optical element 203 is an optical element that reflects or absorbs light in a wavelength range of a second cut wavelength included in the light spectrally divided by the second optical element 203, and transmits light in a second dispersion range. The second cut wavelength preferably includes the wavelength range of the second wavelength range completely or up to the half wavelength. Examples of the second optical element 203 include a short-pass filter, a band-pass filter, and the like. Alternatively, the second optical element 203 may be formed by combining these elements.

Specifically, for example, as illustrated in FIG. 34, the second optical element 203 reflects or absorbs light greater than or equal to the second cut wavelength $\lambda=(780+Y)$ nm. The transmittance of the second optical element 203 decreases at $\lambda=(780-X)$ nm or more, and becomes minimum at $\lambda=(780+Y)$ nm. Light in the second dispersion range is obtained. That is, the second dispersion range is a wavelength range less than $\lambda=(780-X)$ nm from which light greater than or equal to $\lambda=(780+Y)$ nm is excluded. The wavelength range to be the second cut wavelength can be determined to any wavelength range, and the values of X and Y vary depending on the second spectral element to be selected.

As in the first embodiment, the second imaging element 42 is a color image sensor having the second transmission range. The light divided by the second spectral element 201 and transmitted through the second optical element 203 to become the second dispersion range enters the second imaging element 42. The second sensing range, which is a wavelength range of light sensed by the second imaging element 42, is a wavelength range in which the second dispersion range and the second transmission range overlap each other. Specifically, the second sensing range is substantially the same as that in the first embodiment, and is the range indicated by the solid lines in FIG. 14. In the present embodiment, the dotted line in FIG. 14 is the second dispersion range.

The first imaging element 41 and the second imaging element 42 transmit image signals from the sensed light to the image processing unit 61. Note that the functions of the processor device 16 and the image processing unit 61 are the same as those in the first embodiment, and a description thereof will be omitted.

Third Embodiment

In the second embodiment described above, an embodiment in which the light receiving section 15 has the second spectral element, the first optical element, the second optical element, the first imaging element, and the second imaging element has been described. In contrast, in a third embodiment, as illustrated in FIG. 36, a first filter corresponding to the first channel and a second filter corresponding to the second channel are provided in one sensor in the light receiving section 15.

In the first embodiment and the second embodiment described above, the filters provided in the first channel and the second channel are common products or ready-made products. The light receiving section 15 in the third embodiment has a special sensor 300 as illustrated in FIG. 35. In the special sensor 300, a first filter 301 corresponding to the first channel and a second filter 302 corresponding to the second channel are alternately arranged.

The first channel has the first sensing range indicated by the solid line in FIG. 13, and the second channel has the second sensing range indicated by the solid line in FIG. 14. The first channel and the second channel transmit image signals from the sensed light to the image processing unit 61. Note that the functions of the processor device 16 and the image processing unit 61 are the same as those in the first embodiment, and a description thereof will be omitted.

In the first, second, and third embodiments, examples in which the image processing unit 61 and the control unit 59 are connected to the endoscope 12 have been described, and examples of being provided in the endoscope system 10 have been described. However, the present invention is not limited thereto, and other medical apparatuses may be used. As the endoscope 12, a rigid scope or a flexible scope may be used. In addition, some or all parts of the image processing unit 61 and/or the control unit 59 in the endoscope system 10 can be provided in, for example, a medical image processing apparatus that works in collaboration with the endoscope system 10 by communicating with the processor device 16. For example, some or all parts of the image processing unit 61 and/or the control unit 59 in the endoscope system 10 can be provided in a diagnosis supporting apparatus that acquires, directly from the endoscope system 10 or indirectly from PACS (Picture Archiving and Communication Systems), images captured by the endoscope 12. Furthermore, some or all parts of the image processing unit 61 and/or the control unit 59 in the endoscope system 10 can be provided in a medical service supporting apparatus that connects various examination apparatuses such as a first examination apparatus, a second examination apparatus, ..., and an N-th examination apparatus including the endoscope system 10 via a network.

In the first, second, and third embodiments, a hardware configuration of a processing unit that performs various kinds of processing, such as the control unit 59, the image processing unit 61, or the display control unit 66, is any of the following various processors.

Various processors include a CPU (Central Processing Unit), a PLD (Programmable Logic Device), a dedicated electric circuit, and the like. The CPU is a general-purpose processor that functions as various processing units by executing software (programs). The PLD is a processor in which the circuit configuration is changeable after manufacture, such as an FPGA (Field Programmable Gate Array). The dedicated electric circuit is a processor having a circuit configuration that is specially designed to execute various kinds of processing.

One processing unit may be configured by one of these various processors, or may be configured by two or more processors of the same type or different types in combination (e.g., a combination of a plurality of FPGAs or a combination of a CPU and an FPGA). In addition, a plurality of processing units may be configured by one processor. As a first example for configuring a plurality of processing units by one processor, one processor may be configured by a combination of one or more CPUs and software, and this processor may function as a plurality of processing units, as typified by a computer such as a client or a server. As a second example, a processor may be used that implements the functions of the entire system including a plurality of processing units as one IC (Integrated Circuit) chip, as typified by an SoC (System On Chip) or the like. In this manner, various processing units are configured by one or more of the above various processors in terms of hardware configuration.

More specifically, the hardware configuration of these various processors is electric circuitry configured by a combination of circuit elements such as semiconductor elements. The hardware configuration of a storage unit is a storage device such as an HDD (hard disc drive) or an SSD (solid state drive).

REFERENCE SIGNS LIST 10 medical apparatus
12 endoscope
14 light source device
15 light receiving section
16 processor device
18 display
19 console
20 light source unit
22 light source control unit
24 light guide
31 first spectral element
41 first imaging element
42 second imaging element
59 control unit
61 image processing unit
66 display control unit
90 oxygen saturation acquisition unit
80 fluorescent blood-vessel image
82 fluorescent lymphatic-vessel image
91 hemoglobin image generation unit
92 signal ratio calculation unit
93 oxygen saturation calculation table
94 oxygen saturation calculation unit
100 stomach
102 blood-vessel distribution information acquisition unit
104 lymphatic-vessel distribution information acquisition unit
106 StO2 distribution information acquisition unit
108 blood-vessel visualized StO2 information acquisition unit
110 superimposed image generation unit
111 thin blood vessel
112 thick blood vessel
113 thin lymphatic vessel
114 thick lymphatic vessel
120 normal value region
121 hyperoxic region
122 hypoxic region
123 StO2 distribution image
130 normal-light image
131 blood-vessel superimposed image
132 lymphatic-vessel superimposed image
133 vessel superimposed image
134 blood-vessel visualized StO2 image
135 vessel visualized StO2 image
201 second spectral element
202 first optical element
203 second optical element
300 sensor
301 first filter
302 second filter

What is claimed is:

1. A medical apparatus for illuminating a subject and capturing an image of reflected light from the subject, the medical apparatus comprising:
a light source configured to emit illumination light including a first wavelength range;
a light receiving section having a first channel for sensing a first sensing range; and
an image control processor, wherein
the image control processor is configured to acquire an examination image based on light included in the first sensing range, the reflected light includes the first wavelength range and a second wavelength range that is a wavelength range different from the first wavelength range,
the light receiving section has a second channel for sensing a second sensing range that is a wavelength range different from the first sensing range, and has a first spectral element that spectrally divides the reflected light into a first spectral range and a second spectral range different from the first spectral range, a first imaging element having a first transmission range, and a second imaging element having a second transmission range different from the first transmission range,
the first sensing range is a wavelength range that does not overlap with the first wavelength range or overlaps with the first wavelength range up to a half wavelength, and is a wavelength range of a portion where the first spectral range and the first transmission range overlap each other, and
the second sensing range is a wavelength range that does not overlap with the second wavelength range or overlaps with the second wavelength range up to a half wavelength, and is a wavelength range of a portion where the second spectral range and the second transmission range overlap each other.

2. The medical apparatus according to claim 1, wherein
the first wavelength range is a wavelength range necessary for excitation of a fluorescent substance and calculation of oxygen saturation based on a difference in responsiveness to the illumination light between oxyhemoglobin and deoxyhemoglobin,
the first sensing range is a wavelength range including a wavelength range of fluorescence emitted from the fluorescent substance, and
the second sensing range is a wavelength range including the wavelength range necessary for calculation of oxygen saturation.

3. The medical apparatus according to claim 2, wherein
the fluorescent substance receives light including the first wavelength range and emits fluorescence that is light in the second wavelength range,
the first channel is configured to sense the fluorescence, and
the image control processor is configured to:
acquire a fluorescent blood-vessel image based on the fluorescence and a fluorescent lymphatic-vessel image based on the fluorescence as the examination images; and
acquire blood-vessel distribution information from the fluorescent blood-vessel image and lymphatic-vessel distribution information from the fluorescent lymphatic-vessel image.

4. The medical apparatus according to claim 2, wherein the image control processor is configured to:
acquire a hemoglobin image based on light in the wavelength range necessary for calculation of oxygen saturation as the examination image;
calculate the oxygen saturation from the hemoglobin image; and
calculate StO2 distribution information from the oxygen saturation.

5. The medical apparatus according to claim 3, wherein
the light source is configured to emit normal light,
the light receiving section is configured to sense the reflected light obtained by irradiating the subject with the normal light, and the image control processor is configured to:

acquire a normal-light image based on the normal light; and generate at least one of a blood-vessel superimposed image in which the blood-vessel distribution information is superimposed on the normal-light image, a lymphatic-vessel superimposed image in which the lymphatic-vessel distribution information is superimposed on the normal-light image, or a vessel superimposed image in which the blood-vessel distribution information and the lymphatic-vessel distribution information are superimposed on the normal-light image.

6. The medical apparatus according to claim 2, wherein the light receiving section is configured to sense the wavelength range necessary for calculation of oxygen saturation and the wavelength range of the fluorescence, and the image control processor is configured to:

acquire a hemoglobin image based on light in the wavelength range necessary for calculation of oxygen saturation and a fluorescent blood-vessel image based on the fluorescence as the examination images;

calculate the oxygen saturation from the hemoglobin image;

acquire StO2 distribution information from the oxygen saturation;

acquire blood-vessel distribution information from the fluorescent blood-vessel image; and acquire blood-vessel visualized StO2 information from the blood-vessel distribution information and the StO2 distribution information.

7. The medical apparatus according to claim 6, wherein the light source is configured to emit normal light, the light receiving section is configured to sense the reflected light obtained by irradiating the subject with the normal light, and the image control processor is configured to:

acquire a normal-light image based on the normal light; and superimpose the blood-vessel visualized StO2 information on the normal-light image to generate a blood-vessel visualized StO2 image.

8. The medical apparatus according to claim 2, wherein the light source is configured to emit light in the wavelength range necessary for excitation of a fluorescent substance and calculation of oxygen saturation and normal light, and the image control processor is configured to:

acquire a fluorescent blood-vessel image based on the fluorescence, a fluorescent lymphatic-vessel image based on the fluorescence, a hemoglobin image based on the light in the wavelength range necessary for calculation of oxygen saturation, and a normal-light image based on the normal light as the examination images;

calculate the oxygen saturation from the hemoglobin image;

acquire StO2 distribution information from the oxygen saturation;

acquire blood-vessel distribution information from the fluorescent blood-vessel image and lymphatic-vessel distribution information from the fluorescent lymphatic-vessel image;

acquire blood-vessel visualized StO2 information from the blood-vessel distribution information and the oxygen saturation; and superimpose the blood-vessel visualized StO2 information and the lymphatic-vessel distribution information on the normal-light image to generate a vessel visualized StO2 image.

9. A medical apparatus for illuminating a subject and capturing an image of reflected light from the subject, the medical apparatus comprising:

a light source configured to emit illumination light including a first wavelength range;

a light receiving section having a first channel for sensing a first sensing range; and an image control processor, wherein the first sensing range is a wavelength range that does not overlap with the first wavelength range or overlaps with the first wavelength range up to a half wavelength, the image control processor is configured to acquire an examination image based on light included in the first sensing range, the reflected light includes the first wavelength range and a second wavelength range that is a wavelength range different from the first wavelength range, the light receiving section has a second channel for sensing a second sensing range that is a wavelength range different from the first sensing range, the second sensing range is a wavelength range that does not overlap with the second wavelength range or overlaps with the second wavelength range up to a half wavelength, the first wavelength range is a wavelength range necessary for excitation of a fluorescent substance and calculation of oxygen saturation based on a difference in responsiveness to the illumination light between oxyhemoglobin and deoxyhemoglobin, light in the second wavelength range is fluorescence emitted from the fluorescent substance upon receiving light including the first wavelength range, the light receiving section has a first spectral element that spectrally divides the reflected light into a first spectral range and a second spectral range different from the first spectral range, a first imaging element having a first transmission range, and a second imaging element having a second transmission range different from the first transmission range, the first sensing range is a wavelength range of a portion where the first spectral range and the first transmission range overlap each other, and the second sensing range is a wavelength range of a portion where the second spectral range and the second transmission range overlap each other.

10. The medical apparatus according to claim 9, wherein the second transmission range includes a second transmission range A, a second transmission range B, and a second transmission range C, which are different from each other.

11. The medical apparatus according to claim 9, wherein the light receiving section has a second spectral element that spectrally divides the reflected light into at least two or more types of light having a same wavelength range, a first optical element that cuts a first cut wavelength included in the light spectrally divided by the second spectral element to obtain a first dispersion range, a first imaging element having a first transmission range, a second optical element that cuts a second cut wavelength included in the light spectrally divided by the second spectral element and different from the first cut wavelength to obtain a second dispersion range different from the first dispersion range, and a second imaging element having a second transmission range, the first sensing range is a range based on the first dispersion range and the first transmission range, and the second sensing range is a range based on the second dispersion range and the second transmission range.

12. The medical apparatus according to claim 9, wherein the light receiving section has one sensor provided with a first filter corresponding to the first channel and a second filter corresponding to the second channel.

13. A method for operating a medical apparatus for illuminating a subject and capturing an image of reflected light from the subject, the method comprising:

a step of emitting illumination light including a first wavelength range; and a step of acquiring an examination image based on light included in the first sensing range sensed by a first channel included in a light receiving section, wherein the reflected light includes the first wavelength range and a second wavelength range that is a wavelength range different from the first wavelength range, the light receiving section has a second channel for sensing a second sensing range that is a wavelength range different from the first sensing range, and has a first spectral element that spectrally divides the reflected light into a first spectral range and a second spectral range different from the first spectral range, a first imaging element having a first transmission range, and a second imaging element having a second transmission range different from the first transmission range, the first sensing range is a wavelength range that does not overlap with the first wavelength range or overlaps with the first wavelength range up to a half wavelength, and is a wavelength range of a portion where the first spectral range and the first transmission range overlap each other, and the second sensing range is a wavelength range that does not overlap with the second wavelength range or overlaps with the second wavelength range up to a half wavelength, and is a wavelength range of a portion where the second spectral range and the second transmission range overlap each other.

14. A method for operating a medical apparatus for illuminating a subject and capturing an image of reflected light from the subject, the method comprising:

a step of emitting illumination light including a first wavelength range; and a step of acquiring an examination image based on light included in the first sensing range sensed by a first channel included in a light receiving section, wherein the first sensing range is a wavelength range that does not overlap with the first wavelength range or overlaps with the first wavelength range up to a half wavelength, the reflected light includes the first wavelength range and a second wavelength range that is a wavelength range different from the first wavelength range, the light receiving section has a second channel for sensing a second sensing range that is a wavelength range different from the first sensing range, the second sensing range is a wavelength range that does not overlap with the second wavelength range or overlaps with the second wavelength range up to a half wavelength, the first wavelength range is a wavelength range necessary for excitation of a fluorescent substance and calculation of oxygen saturation based on a difference in responsiveness to the illumination light between oxyhemoglobin and deoxyhemoglobin, light in the second wavelength range is fluorescence emitted from the fluorescent substance upon receiving light including the first wavelength range, the light receiving section has a first spectral element that spectrally divides the reflected light into a first spectral range and a second spectral range different from the first spectral range, a first imaging element having a first transmission range, and a second imaging element having a second transmission range different from the first transmission range, the first sensing range is a wavelength range of a portion where the first spectral range and the first transmission range overlap each other, and the second sensing range is a wavelength range of a portion where the second spectral range and the second transmission range overlap each other.

\* \* \* \* \*